US011643625B2

(12) United States Patent
Gobaa

(10) Patent No.: US 11,643,625 B2
(45) Date of Patent: May 9, 2023

(54) HYDROGEL-BASED ORGAN-ON-CHIP MICROFLUIDIC DEVICE

(71) Applicant: INSTITUT PASTEUR, Paris (FR)

(72) Inventor: Samy Olivier Gobaa, Antony (FR)

(73) Assignee: INSTITUT PASTEUR, Paris (FR)

( * ) Notice: Subject to any disclaimer, the term of this patent is extended or adjusted under 35 U.S.C. 154(b) by 427 days.

(21) Appl. No.: 16/954,729

(22) PCT Filed: Dec. 21, 2018

(86) PCT No.: PCT/EP2018/086800
§ 371 (c)(1),
(2) Date: Jun. 17, 2020

(87) PCT Pub. No.: WO2019/122434
PCT Pub. Date: Jun. 27, 2019

(65) Prior Publication Data
US 2020/0385659 A1  Dec. 10, 2020

(30) Foreign Application Priority Data

Dec. 22, 2017 (EP) .................................... 17306926

(51) Int. Cl.
| | | |
|---|---|---|
| C12M 3/00 | (2006.01) |
| C12M 3/06 | (2006.01) |
| C12M 1/12 | (2006.01) |
| C12M 1/00 | (2006.01) |
| C12M 1/34 | (2006.01) |

(52) U.S. Cl.
CPC ............ *C12M 21/08* (2013.01); *C12M 23/16* (2013.01); *C12M 25/14* (2013.01); *C12M 29/10* (2013.01); *C12M 41/40* (2013.01)

(58) Field of Classification Search
CPC .... C12M 251/08; C12M 23/16; C12M 25/14; C12M 29/10; C12M 41/40; G01N 33/4833
See application file for complete search history.

(56) References Cited

U.S. PATENT DOCUMENTS

2012/0190040 A1* 7/2012 Talebpour ......... B01L 3/502715
435/7.1

FOREIGN PATENT DOCUMENTS

| WO | 2010/009307 A2 | 1/2010 |
| WO | 2015/138-34 A2 | 9/2015 |
| WO | 2015/138032 A2 | 9/2015 |
| WO | 2015/157737 A1 | 10/2015 |
| WO | 2017/031167 A1 | 2/2017 |

* cited by examiner

*Primary Examiner* — Michael L Hobbs
(74) *Attorney, Agent, or Firm* — Arrigo, Lee, Guttman & Mouta-Bellum LLP

(57) ABSTRACT

The present invention relates generally to an organ-on-chip microfluidic device (10) comprising a first element (11), a second element (16), and a hydrogel layer (14) which is interposed between the first element and the second element. The shapes and dimensions of the first element, the second element, and the hydrogel layer are determined to enable the hydrogel layer to expand and retract in a given direction in the conditions of use disclosed herein, in particular to mimic organ functions in vitro. The present invention further relates to method of producing the microfluidic device and to application of said microfluidic device in biomedical field, especially for mimicking the architecture and function of organs.

25 Claims, 8 Drawing Sheets

HYDROGEL-BASED ORGAN-ON-CHIP MICROFLUIDIC DEVICE

BACKGROUND OF THE INVENTION

Developing new and powerful in vitro cellular assays is of critical importance to the biomedical industry. In addition to allowing fundamental mechanistic investigations, up-scaled assays are the base of all modern drug discovery and validation pipelines.

Despite considerable efforts, standard assays, based on 2D cell culture and plastic substrates, still suffer from very poor recapitulation of the physiological conditions and thus mostly fail to efficiently predict drug safety and efficacy.

A major explanation for those failures is the lack of physiologically relevant models usable at early stages of drug development. Academic research also faces a comparable lack of models particularly for the study of infectious disease, where the reservoir of many pathogens is exclusively human. Gaining useful insights requires real-time imaging at the cellular level, which is difficult to capture in living animals. In addition, the use of small animal models remains a large ethical problem. Thus, alternative methodologies are highly desirable. Multiple bioengineering approaches including microfluidics, organoid culture and combinatorial screening are currently emerging as viable solutions for bridging the gap between standard in vitro culture assays and animal studies.

In recent years, new cell-based assays with the ambition of providing efficient alternatives to animal testing have emerged. Most noticeably, the development of human organs-on-chip opened new venues for collecting physiologically relevant data with human cells.

The patent application WO 2010/009307 discloses a microfluidic device having a central microchannel separated by one or more porous membranes, e.g. one or more porous PDMS membrane(s), that is/are mounted by physical means. The configuration of said microfluidic device requires additional channels adjacent to a central microchannel in order to create a pressure differential by an indirect pneumatic mechanism between the additional and central microchannels, in response to which the membrane expands or contracts.

The patent application WO 2015/138032 discloses an organomimetic device having microchannels and a membrane that is physically fastened to two portions of said organomimetic device such that said membrane is modulated by a mechanical actuation system physically connected thereto.

The patent application WO 2015/138034 discloses a microfluidic device having two channels with different dimensions separated by a membrane. Said microfluidic device employs a complex design in which the membrane is modulated by an indirect pneumatic mechanism and/or mechanical means by utilizing additional microchannels provided therein.

However, despite large efforts aiming at improving the physiological relevance (3D cell culture, perfusion, mechanical forces) of cellular assays, the existing devices require complex configuration which comprises numerous micro-sized components that are mechanically fastened. Further, the actuation of the device relies on mechanical stimulation by external means or an indirect mechanism. Such devices require high precision mounting/alignment of micro-sized and complex components. Furthermore, the existing devices rely on non-physiological synthetic materials that cannot recapitulate physiological cellular microenvironments.

BRIEF SUMMARY OF THE INVENTION

The present invention relates generally to an organ-on-chip microfluidic device. More specifically, the invention relates to a microfluidic device comprising a first element, a second element, and a hydrogel layer which is interposed between the first element and the second element. The shapes and dimensions of the first element, the second element, and the hydrogel layer are determined to enable the hydrogel layer to expand and retract in a given direction in the conditions of use disclosed herein, in particular to mimic organ functions in vitro. The herein disclosed device allows for the development of physiologically relevant, genetic, biochemical, cellular, tissue or organ-based assays. The present invention further relates to method of producing the microfluidic device and to application of said microfluidic device in biomedical field, especially for mimicking the architecture and function of organs.

Particular features of the invention will be illustrated in the following figures and examples. The features disclosed therein also define embodiments of the invention as described above.

DETAILED DESCRIPTION OF THE INVENTION

Figure 1A:
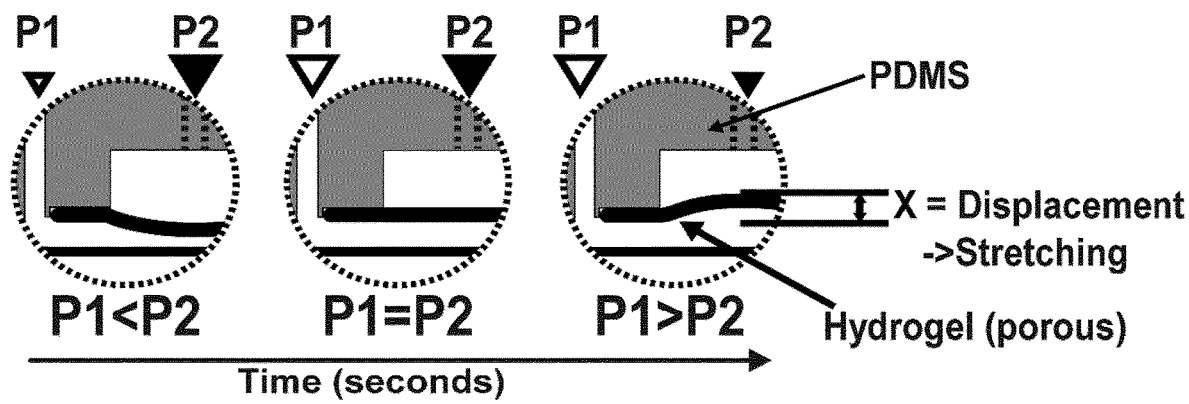
FIG. 1: (A-B) The concept of microfluidic device based on Hydraulically Actuated Hydrogel Layer (HAHL); the hydrogel thin layer is actuated over time by the differential pressure between the upper and the lower channel. This actuation is possible because of the covalent bonding of the hydrogel to the first element. Actuation profiles are directly under the control of the HAHL-device users by varying the hydraulic pressure over time. (C) As an early proof of concept, HAHL-device was seeded with Caco2/E-Cad:GFP epithelial cells in the upper channel (P1) and with wild type HUVECs in the lower channel (P2). Scale bar 200 microns. Dotted rectangle: insert location. Dotted lines: limit of the upper microfluidic channel. (D) Preliminary results with early HAHL-microfluidic device. A closed circuit was used for the perfusion of HAHLs over several days and assessment of hydrogel layers deformation, using 2D microscopic observations of cells placed on top of the actuated hydrogels. (E) Estimation of PEG-Fibronectin (PEG-Fn) mechanotransducer deformation based on the microscopic analysis of periodic cell displacement. Error bars=standard deviation over 3 features. Visualization of C2C12 cells growing in 2D on the PEG-Fn hydrogel layer. (F) Differential deformation in two regions of a hyaluronan-gelatin hydrogel grafted on a thin PEG mechanotransducer. The star represents a point where circular deformation was so large that it caused beads above the center of the channel to leave the focal plane, thus forcing to use points where the small-angle approximation does not hold anymore. R2=coefficient of determination for linear regressions. Error bars=standard deviations based on the analysis of 5 features (pairs of beads).

The present invention provides an advanced organ-on-chip microfluidic device at recapitulating human organ microenvironment, especially the endothelium/epithelium interface in many mechanically active compartments or tissues by combining both microfluidic and hydrogel technologies.

The hydrogel-based devices enable culturing cells on physiologically relevant substrates (hydrogels) with tunable mechanical properties while the substrates (hydrogels) are mechanically stimulated by pressure exerted by a fluid (liquid or gas) directly onto the substrates (hydrogels) to expand or retract, in particular cyclically expand or retract, in order to mimic physiological conditions, such as heart beating, breathing, peristaltic motion of the intestine or muscle stretching. In addition, the use of hydrogels that are sensitive to proteolytic degradation enables the seeded cells to invade and closely interact with the provided soft matrix. In contrast to existing approaches, the present invention offers improved cellular assays which enable to precisely recapitulate biophysically and biochemically the extracellular matrix interface of the target tissues.

The invention accordingly provides a microfluidic device that relies on the actuation of hydrogel layer capable of mimicking or recapitulating physical and/or physiological parameters of biological compartments or tissues, in particular of human organs in vitro.

The present invention relates to a microfluidic device comprising:

a) a first element comprising one or more types of chemical functional groups on its surface, wherein said one or more types of the chemical functional groups are comprised in molecules covalently bound to said surface;

b) a hydrogel layer having a first face and a second face located opposite to each other, said hydrogel layer comprising one or more types of chemical functional groups, at least one type of said chemical functional groups is effective to react with at least one type of the chemical functional groups comprised in the molecules covalently bound to the surface of the first element; and c) a second element, wherein the hydrogel layer is interposed between the first element and the second element in a given axis substantially perpendicular to the hydrogel layer and wherein the first element, the second element and the hydrogel layer have shapes and dimensions determined to delineate and/or form at least one microchannel between the first element and the first face of the hydrogel layer and at least one cavity between the second element and the second face of the hydrogel, said at least one microchannel and said at least one cavity being arranged relative to each other so that said given axis intercepts both said at least one microchannel and said at least one cavity and, wherein at least one type of said chemical functional groups comprised in the molecules covalently bound to the surface of the first element and at least one type of the chemical functional groups of the hydrogel layer are covalently bound to each other.

As used herein, the term "element" refers to a part, block, body or substrate of the microfluidic device that is more rigid relative to the hydrogel layer. Accordingly, the elastic modulus of the first element or the second element is higher than that of the hydrogel layer and generally high enough to enable selective stimulation of the hydrogel layer when a desired degree of pressure is applied as a result of a fluid introduced in the microchannel(s) of the first element and/or cavity(ies) of the second element. Such direct stimulation mechanism does not require any additional channels adjacent to the microchannel(s) or cavity(ies), thus the device is relatively simple to produce. In a particular embodiment the element is composed of a rigid material, in particular a flat piece of rigid material.

As used herein, the term "surface" does not necessarily represent the entire surface or the entire outer surface of the first element or the second element, but encompasses a portion of an entire surface or a portion of the outer surface thereof. In a particular embodiment, the surface is the entire surface of said element(s) or is essentially the entire surface of said element(s).

In a particular embodiment, the molecules covalently bound to the surface of the first element form a monomolecular layer. A monomolecular layer refers to a single layer of molecules. The term "monomolecular layer" can be used interchangeably with the terms "monomolecular film" or "monolayer of molecules", and may be referred as a "self-assembled monolayer". In a preferred embodiment, the molecules are of one type and accordingly have the same molecular formula.

The term "chemical functional groups" is used as a plural noun to indicate two or more "chemical functional group", which is commonly referred as "functional groups" in the field of organic chemistry. A chemical functional group or, simply, a functional group refers to a specific group of atoms that determines chemical properties and reactivity. In a particular embodiment, the chemical functional group is within a molecule or compound and determines chemical properties or reactivity of said molecule or compound. Different types of chemical functional groups consist of different groups of atoms.

The molecule covalently bound to a surface of said first element comprises at least one type of functional groups that are available to undergo a chemical reaction.

The molecule, in its original structure (i.e. prior to covalently bonding with the first element or the hydrogel layer), preferably comprises two end groups (i.e., groups of atoms or chemical functional groups), each end comprising one or more chemical functional groups. The functional group on one end of the molecule is covalently bound to the surface of the first element, and the functional group on the other end of the molecule is covalently bound to at least one type of functional groups of the hydrogel layer.

As used herein, the term "cavity" refers to a hollow space, which is free of any of the material constituting the elements and hydrogel. In one embodiment, a cavity refers to a channel, especially a microchannel, which is extended along a face of the hydrogel layer and intended to allow a passage or circulation of a liquid or gas. For example, the liquid encompasses a cell culture medium. The two ends of the channel serve as an inlet and an outlet of the liquid or gas. In another embodiment, a cavity refers to a chamber or reservoir which can contain a liquid without circulation of said liquid. In particular, the cavity diameter (parallel to the hydrogel layer) is in a range from 10 mm to 40 mm, and the height (perpendicular to the hydrogel layer) is in a range from 10 µm to 20 mm.

The term "microchannel" refers to a channel with dimensions, except its length, (e.g. width and height) below 1 mm. In particular, the width (parallel to the hydrogel layer) and the height (perpendicular to the hydrogel layer) of a microchannel are in a range from 10 µm to 999 µm. The length (parallel to the hydrogel layer) of the microchannel is extended along the first face of the hydrogel layer and intended to allow a passage or circulation of a liquid. Said length of the microchannel is comprised in a range between 0.1 mm and 15 mm. The two ends of the microchannel serve as an inlet and an outlet of the liquid or gas.

As used herein, the term "hydrogel layer" refers to a layer that may be regarded as globally flat layer, such as a sheet of hydrogel of any shape, for example, rectangle, circle or square, when viewed from the first face or the second face of the hydrogel layer. Said two faces are separated by the thickness of said hydrogel layer, said thickness being smaller than any other dimensions of the hydrogel layer. The term "hydrogel" encompasses a polymeric network of crosslinked hydrophilic polymers or macromonomers able to swell by absorbing or trapping water molecules within its structure. In one embodiment, the thickness of the hydrogel layer is uniform across its entire surface. In another embodiment, the thickness of the hydrogel layer is non-uniform across its entire surface, especially across the region where the first face of the hydrogel faces the microchannel(s) and the second face of the hydrogel faces the cavity/cavities. For example, the hydrogel layer may have varying thickness or lower thickness in said region relative to the rest of the hydrogel layer.

The inventors have advantageously designed a new organ-on-a-chip platform that relies on the actuation of hydrogel layer(s). The device comprising hydrogel layer(s) chemically bound thereto via formation of covalent bonds enables the hydrogel layer to expand or retract in response to a difference in fluid pressure between a microchannel on one side (i.e. first face) of the hydrogel layer and a cavity on the opposite side (i.e. second face) of the hydrogel layer. The technical advantages associated with such device assembly include reduced complexity of mechanical manipulation of components and improved long-term stability of the device. In particular, the irreversible covalent attachment of the hydrogel layer contributes to a simplified and direct actuation mechanism of the device while reducing the risk of accidental disassembly, rupture or leakage. The device design further ensures that no pressure is applied to the parts of the hydrogel layer that are not meant to be actuated (i.e. the hydrogel layer is not squeezed within the device between two elements/components); the only pressure experienced by the hydrogel layer is caused by the actuation of hydrogel layer based on the differential fluid pressure as mentioned above. The invention demonstrates for the first time how hydrogel can be used as a dynamic force transducer in a biological setup.

The hydrogel layer disclosed herein is capable of reproducing the mesenchyme (also named Stroma). Said hydrogel layer is not inert; for example, it is sensitive to proteolytic degradation. Said hydrogel layer further allows creating chemical gradients between the microchannel(s) and the cavity(ies) located on the opposite sides of the hydrogel layer.

According to the invention, the arrangement of the microfluidic device disclosed herein enables actuation and deformation of the hydrogel layer in a direction toward at least one microchannel between the first element and the first face of the hydrogel layer or toward at least one cavity between the second element and the second face of the hydrogel, upon stimulation of the hydrogel layer, such as applying differential fluid pressure between said at least one microchannel and said at least one cavity that are arranged relative to each other in a given axis that intercepts both said at least one microchannel and said at least one cavity.

As used herein the term "actuation of hydrogel layer" refers to an act of inducing the hydrogel layer to move or elastically deform.

As used herein, the term "deformation of hydrogel layer" refers to a reversible alteration or change of the form of the hydrogel layer, especially by expanding or retracting of the hydrogel layer. The deformation is especially reversible and may be ceased with the stimulation of the hydrogel layer.

The action of expanding and retracting is characterized by cyclic stretching of the hydrogel layer as the hydrogel layer experiences pressure due to a fluid that exerts pressure normal to the contacting surface (first or second face) of the hydrogel, which causes the hydrogel layer to bend or flex. In particular, the pressure experienced by the hydrogel layer is due to the fluid pressure difference between the microchannel on the first face of the hydrogel and the cavity on the second face of the hydrogel.

As used herein, the term "stimulation of hydrogel layer" refers to the application of a stimulus, which actuates the hydrogel (i.e. putting the hydrogel into motion) to move or elastically deform by expanding or retracting in response thereto, e.g., a pressure difference between the microchannel delineated by the first element and the first face of the hydrogel layer and the cavity between the second element and the second face of the hydrogel layer.

Said pressure difference, in particular fluid pressure difference, is created by a fluid (gas or liquid) flowing in the microchannel on the first face of the hydrogel and a fluid (gas or liquid) flowing in the cavity on the second face of the hydrogel. Said fluids exert varying amount of pressure on the first face and the second face of the hydrogel layer by adjusting the flow rate of a liquid and/or the pressure of a gas.

The actuation of hydrogel layer is thus driven by varying either liquid flow rate or gas pressure in the microchannel(s) and/or the cavity(ies).

The fluid in the microchannel(s) on the first face of the hydrogel layer and the fluid in the cavity(ies) on the second face of the hydrogel layer may be flowing in the same direction or in the opposite directions.

In one embodiment, the fluid in at least one of the microchannels on the first face of the hydrogel layer or at least one of the cavities on the second face of the hydrogel layer is a gas. The use of a gas for applying a pressure to the hydrogel layer may enable the reconstruction of, for example, a lung alveolus.

In one embodiment, the fluid in at least one of the microchannels on the first face of the hydrogel layer or at least one of the cavities on the second face of the hydrogel layer is liquid. The use of a liquid, allows a better control of the pressure within the cavity and therefore allows a good control of the modulation (i.e. elastic deformation) of the hydrogel layer, due to the low compressibility of a liquid as compared to a gas.

In a preferred embodiment, the fluids in all microchannels and cavities comprised in the device are liquids.

In one embodiment, the first element is physically in contact with the first face of the hydrogel layer and the second element may or may not be in contact with the second face of the hydrogel layer.

In another embodiment, the second element is physically in contact with the first element and the hydrogel layer is physically in contact with one or both of the first element or the second element.

The contact between the first and the second elements does not exert any pressure on the hydrogel layer in all embodiments of the invention. Said first and second elements are tightened with one another, either directly or indirectly, such that the hydrogel layer is hermetically housed within a fluid circuit configured means for creating a pressure differential pressure between said at least one microchannel and said at least one cavity.

In a particular embodiment, a surface of the second element facing the hydrogel layer comprises one or more types of chemical functional groups and at least one type of said chemical functional groups is covalently bound to at least one type of the chemical functional groups of the hydrogel layer. Said one or more types of chemical functional groups are comprised in molecules which are covalently bound to a surface of said second element. Said molecules comprising one or more types of chemical functional groups may or may not be identical to the molecules comprising one or more types of chemical functional groups which are covalently bound to a surface of the first element. Accordingly, said one or more types of chemical functional groups on the surface of said second element may or may not be identical to said one or more types of chemical functional groups on the surface of said first element.

In another embodiment of the invention, the device may be configured in such a way that at least one of the first and second element is made of at least two pieces, i.e. a first piece and a second piece. For example, the second piece of the first element is located between the first piece of the first element and the second element. The second piece of the first element is configured in such a way that a first face of the second piece of the first element is in contact with the first piece of the first element, and a second face of the second piece of the first element located opposite the first face is in contact with the second element. In another similar example, the second piece of the second element is located between the first piece of the second element and the first element. The second piece of the second element is configured in such a way that a first face of the second piece of the second element is in contact with the first piece of the second element, and a second face of the second piece of the second element located opposite the first face is in contact with the first element.

In one embodiment, the second piece of the first or second element functions as a spacer element that creates one or more cavities between the second face of the hydrogel layer and the second element. In another embodiment, the second piece of the first or second element is an annular element having one or more hollow structures (e.g. hollow circle, square or rectangle). For example, said second piece is an annular sealing element of any shape, such as circular, square or rectangular, in particular a ring having a section that is circular, i.e. an O-ring, that prevents leakage of a liquid or gas between the second face of the hydrogel layer and the second element. In a particular embodiment, the second piece of the first or second element has dual functionality in that it acts as a spacer for creating one or more cavities between the second face of the hydrogel layer and the second element as well as an annular sealing element that prevents leakage of a liquid or gas between the second face of the hydrogel layer and the second element.

In one embodiment, the first or second element or both elements comprise(s) at least one depression or indentation therein, in particular in at least one flat side or surface thereof. Said at least one depression or indentation is produced by various techniques including, but not limited to, photolithography, laser ablation, micromilling, etching, or molding, and may have any shape or dimensions. In a particular embodiment, the depression or indentation comprises at least one wall perpendicular to the surface in which said depression or indentation is comprised, defining the height or depth of said depression or indentation.

Said at least one depression or indentation comprised in the first element and second element may have the same or different shape and dimensions. In one embodiment, said at least one depression or indentation comprised in the second element which forms/delineates at least one cavity between the second face of the hydrogel layer and the second element has a wider width compared to the width of said at least one depression or indentation comprised in the first element which forms/delineates at least one microchannel between the first face of the hydrogel layer and the first element.

The term "depression" or "indentation" encompasses a groove. In a particular embodiment, the first element comprises at least one groove that is covered by the hydrogel layer so as to form said at least one microchannel.

The term "groove", as used herein refers to a long narrow depression or indentation in a surface, ranging from nanometer to centimeter, in particular micrometer, which is produced by various techniques including, but not limited to, photolithography, laser ablation, micromilling, etching, or molding. The groove may be of any shape along its direction of elongation and may have a section of any shape. For example, the groove may be curved but is preferably rectilinear, i.e. straight, and may have a curved or rectangular section.

In a specific embodiment, one side of the first element comprises a groove which is covered by a hydrogel layer forming a microchannel. The surface area of the first face of the hydrogel layer is dimensioned to cover the groove comprised in said side of the first element. Said first face of the hydrogel layer is covalently bound to said side of the first element comprising the groove on two surfaces separated by the width of said groove. The surface areas of the two surfaces separated by the width of said groove are sufficient to allow the covalently bound hydrogel layer to be kept attached during use (i.e. actuation by fluid pressure differential) of the device.

According to an embodiment, at least one of the first element and second element comprises a recess within which the hydrogel layer is mounted. The hydrogel layer may cover at least one groove formed onto said surface of said first element so as to form at least one microchannel. Also, said recess may be formed on said first element and may comprise a bottom having said at least one groove.

In a particular embodiment, the recess opens out on an annular surface that is applied onto said second element to form said at least one cavity located, relative to said hydrogel layer, opposite to said at least one microchannel.

The first element and the second element comprise each a material or any combinations of materials selected from, but not limited to, silicone rubber (i.e. polysiloxane), crystalline silicon, poly(dimethylsiloxane) (PDMS), silica (e.g., quartz and glass), thermoplastics (e.g., poly(methyl methacrylate) (PMMA), polycarbonate (PC), polystyrene (PS), poly(ethylene glycol) diacrylate (PEGDA), polyurethane (PU), perfluorinated compounds (e.g., perfluoroalkoxy (Teflon PFA) and fluorinated ethylenepropylene (Teflon FEP)), and polyolefins (e.g., cyclic olefin copolymer (COC), cyclic olefin polymer (COP), cyclic block copolymer (CBC), and polyvinyl chloride (PVC)), polyimide (PI), poly(lactic-co-glycolic acid) (PLGA), thermoset polyester (TPE), off-stoichiometry thiol-ene (OSTE), transparent ceramics such as aluminum oxide ($Al_2O_3$), spinel ($MgAl_2O_4$), yttria alumina garnet (YAG), and neodymium-doped yttria alumina garnet (Nd:YAG), and paper (e.g. transparent or translucent paper). In a particular embodiment, the first element and the second element comprise silica (e.g., quartz and glass). In another embodiment, the first element and the second element comprise poly(dimethylsiloxane) (PDMS), thermoplastics (e.g., poly(methyl methacrylate) (PMMA), polycarbonate (PC), polystyrene (PS), polyurethane (PU), perfluorinated compounds (e.g., perfluoroalkoxy (Teflon PFA) and fluorinated ethylenepropylene (Teflon FEP)), and polyolefins (e.g., cyclic olefin copolymer (COC), cyclic olefin polymer (COP), cyclic block copolymer (CBC), and polyvinyl chloride (PVC)), poly(lactic-co-glycolic acid) (PLGA), thermoset polyester (TPE).

The first element and the second element may or may not comprise an identical material. In a particular embodiment, the first and the second elements are made of the same material. In another embodiment the first and the second elements are made of different materials.

In a particular embodiment, the first element and/or the second element is made of a material that is suitable to enable detection of signals created when using the microfluidic device, for example by optical microscopes, fluorescence microscopes, or electron microscopes. Said material especially enables detection of at least one electromagnetic wavelength that would be emitted by a component (e.g. biological, chemical or biochemical compound) within said at least one microchannel and/or said at least one cavity and/or the first or second face of the hydrogel layer or the bulk of the hydrogel. In particular, said detection is detection of fluorescence.

In a preferred embodiment, at least one of the first element, the second element or all of said elements comprise(s) a transparent or translucent material selected from the group of materials listed above.

In a further preferred embodiment, the first element comprises or consists of PDMS. In another preferred embodiment, the second element comprises or consists of silica.

In a particular embodiment, the chemical functional groups comprised in the molecules covalently bound to the surface of the first element or the second element comprise thiol (—SH) groups. The molecules that covalently bind to the surface of the first element or the second element may have general chemical formula, $X(CH_2)n\ SiY_3$, which contains reactive functional groups X and Y. The X is a functional group, for example mercapto group, that is exposed on the surface of the first element, the second element or both elements, which is capable of undergoing chemical reaction, in particular with a functional group, such as vinylsulfone group, of the hydrogel layer to form covalent bonding; the n is an integer of 1 to 3; and the Y is a functional group such as methoxy, ethoxy, and methyl. The Y is the group that is covalently bound to the surface of the first element or the second element. Examples of such molecules include, but not limited to, (3-Mercaptopropyl) trimethoxysilane, (3-Mercaptopropyl)triethoxysilane, and (3-Mercaptopropyl)methyldimethoxysilane. In a particular embodiment, said molecules comprise or consist of (3-Mercaptopropyl) trimethoxysilane (MPS).

In a particular embodiment, the chemical functional groups comprised in the molecules covalently bound to at least a portion of the surface of the first element or the second element comprise thiol groups and the chemical functional groups comprised in the hydrogel layer comprise vinylsulfone groups. In another embodiment, the chemical functional groups comprised in the molecules covalently bound to at least a portion of the surface of the first element or the second element comprise thiol groups and the chemical functional groups comprised in the hydrogel layer comprise acrylate or maleimide groups or any thiol-reactive functional groups.

In a particular embodiment, the hydrogel layer has an elastic modulus (shear modulus) in a range from 1 kPa to 50 kPa. In a preferred embodiment, the shear modulus of the hydrogel layer is in the range from 10 kPa to 30 kPa. The choice of the value of the elastic modulus (shear modulus) depends on the width of the microchannel or cavity, the density and thickness of the hydrogel layer, the desired degree of deformation, the presence of cells within or on the hydrogel layer (the choice of the stiffness of the hydrogel depends on the cultured cells), and the temperature of the device during use. The shear elastic modulus within the above mentioned range advantageously enables a stretching (i.e. expanding or retracting) of the hydrogel layer up to 25% when used. The degree of stretching of the hydrogel layer is quantified by: i) comparing the area of the cell that is seeded on the hydrogel layer before and after applying hydraulic pressure, or ii) embedding fluorescent microspheres (e.g. polystyrene beads) within the hydrogel and measuring the variation of distance between the beads by traction force microscopy (TFM).

The term "elastic modulus" refers to a numerical constant which describes the ratio of exerted force upon a given area of a material, such as hydrogel, to the deformation of the material due to said exerted force. The values of elastic modulus disclosed herein refers to shear modulus or modulus of rigidity, which describes the stiffness of material and is defined as the ratio of shear stress to the shear strain. The elastic modulus (shear modulus) of the hydrogel layer is measured by a technique known in the field, such as a microrheometer. For example, a method using a microrheometer is described in "*Substrate elasticity modulates the responsiveness of mesenchymal stem cells to commitment cues.*" Gobaa S, Hoehnel S, Lutolf M P., Integr Biol (Camb). 2015 October; 7(10):1135-42. (see e.g. paragraph "Measurements of substrate stiffness"). Those skilled in the art are able to determine the parameters suitable for the measurement of elastic modulus.

In a particular embodiment, the hydrogel layer has a thickness in the range from 30 μm to 500 μm, and more preferably from 150 μm to 350 μm, in particular 170 μm to 340 μm, more particularly 150 μm to 200 μm.

In a particular embodiment, the device comprises two or more layers of hydrogel. For example, the device may comprise 1 to 3 layers of hydrogel, each hydrogel layer having thickness in the range from 30 μm to 500 μm. In one embodiment, the total thickness of one or more hydrogel layers is in a range from 170 μm to 340 μm. In another embodiment, the thickness of one or more hydrogel layers is 170 µm. Two or more layers of hydrogel are advantageously linked together by chemical bonds (i.e. covalent bonds).

The hydrogel layer comprises a polymeric matrix comprising or consisting of polymeric or polymerized network of one or more macromonomers having hydrophilic functional groups attached to the polymeric backbone or one or more macromonomers of hydrophilic nature. In a particular embodiment, the polymeric matrix comprises polyethylene glycol (PEG), in particular functionalized PEG. In a preferred embodiment, said polymeric matrix comprises a polymerized network of two different functionalized PEG macromonomers (i.e. one PEG macromonomer containing one functional group and another PEG macromonomer containing another functional group).

In a particular embodiment, the PEG hydrogel concentrations are in a range from 2.5% to 10% (w/v). In a preferred embodiment, the PEG hydrogel concentration is in a range from 5% to 10% (w/v). In a further preferred embodiment, the PEG hydrogel concentration is 5% (w/v).

In a preferred embodiment, the polymeric matrix of said one or more macromonomers comprises vinylsulfone groups, thiol groups or both groups. The polymeric matrix of the hydrogel layer is preferably formed by crosslinking PEG-SH macromonomers, in particular star-shaped or multi-arm PEG-SH macromonomers, and PEG-VS macromonomers, in particular star-shaped or multi-arm PEG-VS macromonomers, via a reaction, in particular Michael-type addition reaction, between SH groups and VS groups. In such case, the covalent linkage between SH groups and VS groups crosslinks the macromonomers to form the polymeric matrix. In a particular embodiment, the polymeric matrix comprises unsaturated SH groups and/or unsaturated VS groups.

In another embodiment, the polymeric matrix comprising PEG comprises polypeptides as crosslinkers between PEG macromonomers, for example by using methods disclosed in Lutolf and Hubbel, 2003. Said polymeric matrix comprising PEG macromonomers crosslinked via polypeptides are sensitive to various proteases, including metalloproteinases (MMPs).

The term "polymeric matrix" refers to a polymer network or polymerized network formed by crosslinking of macromonomers. According to the disclosure of the invention, two or more macromonomers containing different functional groups are crosslinked to form said polymeric matrix via formation of covalent bonds between different functional groups susceptible to react with each other. The functional groups remain unsaturated (i.e. available for a reaction) until the crosslinking is complete, given that the stoichiometric molar ratio (i.e. equimolar quantities) of the two reactive functional groups is fulfilled. In a particular embodiment, the stoichiometric molar ratio of the two reactive functional groups is not fulfilled, resulting in unsaturated functional groups in the polymeric matrix which are added in a molar excess. The functional groups serve as crosslink junctions in the formation of the polymeric matrix.

The term "macromonomer" refers to a macromolecule, such as polymer or oligomer, which acts as a precursor for subsequent crosslinking that leads to a formation of a polymer or macromolecule having a higher molecular weight. The macromonomer may have a variety of structures/architectures, including linear, cyclic, and branched structures/architectures (e.g. star-shaped, comb- or brush-shaped, hyperbranched, dendritic, H-shaped, long-chain branched, dumbbell-shaped, etc.).

In a particular embodiment, the hydrogel layer comprises an amount of thiol groups in a molar excess in a range of 0 to 10% relative to vinylsulfone groups. In such case, there exist unsaturated thiol groups in the bulk and on the surface of the hydrogel layer that are susceptible to a chemical reaction, and are especially available for binding to cell adhesion molecules, in particular cell adhesion molecules coupled with a crosslinker that covalently binds to said unsaturated thiol groups.

In a particular embodiment, the hydrogel layer contains 1.2 mM of free thiol groups in order to further immobilize proteins or peptides.

In a particular embodiment, the hydrogel layer comprises microstructures or micropatterns. Topographically structured stamps (for example those made of PDMS, silicones, glass, plastics, ceramics or metals) produced by photolithography, micromilling or molding may be used to create microstructures or micropatterns on at least a portion of the surface of the hydrogel layer in order to recapitulate the structure of the target organ, in particular the crypt/villi of the intestine. These stamps can be used in two ways:

1—soft-embossing the surface of a partially crosslinked hydrogel (Kobel et al. 2009). In brief, this technique requires pressing the structured stamp onto a partially crosslinked hydrogel. The negative of the pressed structures is permanently transferred to the hydrogel upon the completion of the crosslinking reaction.

2—molding the structure while casting the hydrogel layer (Lutolf et al. 2009). This technique entails sandwiching the hydrogel precursor solution between the stamp and a flat Teflon or silanized glass slide. The thickness of the used spacer determines the thickness of the produced structured hydrogel layer.

The microfluidic device of the invention is suitable and intended for seeding of cells, in particular mammalian cells with a view to perform assays including structural or functional assays relative to the observation of growth, expansion, differentiation, or biological activity of the cells or the synthetically organized tissue. Accordingly, the microfluidic device allows the seeded cells to be maintained on and/or within the hydrogel layer through attachment molecules such as adhesion molecules. The use of hydrogels that are sensitive to proteolytic degradation enables the seeded cells to invade and closely interact with the provided soft matrix.

In a particular embodiment, at least one type of cell adhesion molecules is attached (e.g. covalently or non-covalently attached) to at least one of the first face of the hydrogel layer, the second face of the hydrogel layer, the bulk of the hydrogel layer or any combination thereof. The term "bulk of hydrogel layer" refers to the part within the thickness of the hydrogel layer between the first face and the second face of the hydrogel layer. Said at least one type of cell adhesion molecules are allowed to attach to the hydrogel layer by: i) introducing into the bulk of the hydrogel layer during the steps of the polymerization of said hydrogel layer (e.g. can be added to the mixture of PEG macronomoners), and/or ii) introducing a liquid containing cell adhesion molecules into the microchannel(s) or cavity(ies).

Preferably, the cell adhesion molecules, such as cell adhesion proteins are covalently attached to at least one type of the chemical functional groups of the hydrogel layer. In a particular embodiment, the cell adhesion molecules are covalently attached to the thiol groups of the hydrogel layer.

In a particular embodiment, the cell adhesion molecules are tagged or modified to improve their adhesion function with respect to the cells. In a particular embodiment, they are tagged with fc antibody fragment or modified with a heterobifunctional protein crosslinking reagent, such as a heterobifunctional NHS-PEG-maleimide linker. This linker is first reacted with any molecule of interest having primary or secondary amines in its structure (amino acids, peptides, proteins) at a physiological pH. This will allow for the formation of an amide bond between the molecule of interest and the heterofunctional linker. This way, and by adjusting the stoichiometric ratio between the molecule of interest and the heterofuctional linker, we can create a molecule of interest with variable maleimide functions (typically between 1 and 20).

In a particular embodiment, the cell adhesion molecules modified with a heterobifunctional protein crosslinking reagent are attached to the thiol groups of the hydrogel layer via formation of covalent bonding between said heterobifunctional protein crosslinking reagent and said thiol groups of the hydrogel layer.

In another embodiment, the cell adhesion molecules modified with an Fc antibody fragment are adsorbed to the hydrogel layer (affinity based) containing ProteinA or ProteinG or any other molecule having an affinity for Fc fragments. Similar to the former embodiment, ProteinA is covalently bound to a heterobifunctional protein crosslinking reagent, which is covalently attached to the thiol groups of the hydrogel layer. In this particular embodiment, the assayed fluid provided in the microchannel(s) or cavity(ies) does not contain antibodies or Fc fragments of antibodies.

In a particular embodiment, the cell adhesion molecules comprise any one of fibronectin, collagen, laminin or any combination or fractions thereof. In a particular embodiment, cells are deposited on the first face of the hydrogel layer that was previously functionalized with cell adhesion molecules, especially cell adhesion proteins or peptides. The same operation can be performed on any one of the second face of the hydrogel layer, in the bulk of the hydrogel layer or any combination thereof. In a particular embodiment, any one of the first face of the hydrogel layer, the second face of the hydrogel layer, the bulk of the hydrogel layer or any combination thereof contains identical or different types of cells.

In a particular embodiment, the cells form one or more layers.

The cells comprise human cells. Said human cells may be selected from the group consisting of primary cells, immortalized cell lines, epithelial cells, endothelial cells, mesenchymal stem cells, brain cells, muscle cells, immune cells, induced pluripotent stem cells, embryonic stem cells. All adherent cells, presenting integrin receptors at the surface can be seeded and attached to the two surfaces (i.e. the first and second faces) of the hydrogel layer. Non-adherent and adherent cells can be encapsulated in the bulk of the hydrogel.

In a particular embodiment, the device may be used to mimic a mesenchyme wherein cells of mesenchymal origin such as, but not exclusively, fibroblasts, bone marrow derived mesenchymal primary cells, and/or intestinal stromal cells are allowed to reside and migrate easily (e.g. circulate or reside).

In an example, TC7 CaCo2 epithelial cells are seeded on the first face of the hydrogel layer and HUVECs (Human umbilical vein endothelial cells) are seeded on the second face of the hydrogel layer.

In a particular embodiment of the invention, the microfluidic device mentioned above is an integrated device that comprises:

a hydrogel layer hydrogel layer having a first face and a second face located opposite to each other, a first element and a second element, wherein the hydrogel layer is interposed between a first element and a second element in a given axis substantially perpendicular to the hydrogel layer and wherein the first element, the second element and the hydrogel layer have shapes and dimensions determined to delineate at least one microchannel between the first element and the first face of the hydrogel layer and at least one cavity between the second element and the second face of the hydrogel, said at least one microchannel and said at least one cavity being arranged relative to each other so that said given axis intercepts both said at least one microchannel and said at least one cavity; and wherein the integrated device comprises means for creating a pressure differential between said at least one microchannel and said at least one cavity.

Said means may comprise pumps, valves and pipes to transfer a liquid from a storage unit or a gas from a compressed gas cylinder to said at least one microchannel and said at least one cavity. Said means may further comprise flow meters, pressure gauges, sensors, indicators and switches.

The device may comprise conduits that pass through the first element and/or the second element to introduce and/or withdraw a liquid or gas to/from said at least one microchannel and/or said at least one cavity.

In a particular embodiment, the microfluidic device further comprises conduits passing through the first element and the hydrogel layer to introduce and/or withdraw a liquid or gas to/from said at least one cavity.

Preferably, the connections to the conduits are made on the same side of the microfluidic device.

In a particular embodiment, at least one of said first element and said second element is transparent to at least one electromagnetic wavelength that would be emitted by a component (e.g. biological, chemical or biochemical compound) within said at least one microchannel and/or said at least one cavity, in order to enable, for example visual or signal detection using a microscope.

In a particular embodiment, said first element, second element and hydrogel layer are mounted on a holder between an abutment of the holder and a clamping element, which is preferably removable, such as a nut.

The invention also relates to a method for producing a microfluidic device according to the invention comprising:
a) producing or providing the first element and the second element;
b) functionalizing a surface of the first element, such as PDMS, with molecules comprising one or more types of chemical functional groups;
c) optionally functionalizing a surface of the second element, such as PDMS, with molecules comprising one or more types of chemical functional groups;
d) producing or providing a hydrogel layer containing one or more types of chemical functional groups effective to react with at least one type of the chemical functional groups of the molecules on the surface of the first element or the second element or both elements;
e) placing the hydrogel layer between the first element and the second element; and
f) allowing at least one type of the chemical functional groups of the molecules on the surface(s) of the first element, the second element or both elements to covalently react with at least one type of the chemical functional groups of the hydrogel layer.

In another embodiment of the invention, said method for producing a microfluidic device according to the invention comprises the steps of a) producing or providing a first piece of the first element, a second piece of the first element, and the second element;
b) functionalizing a surface of the first piece of the first element, such as PDMS, with molecules comprising one or more types of chemical functional groups;
c) optionally functionalizing a surface of the second element, such as PDMS, with molecules comprising one or more types of chemical functional groups;
d) producing or providing a hydrogel layer containing one or more types of chemical functional groups effective to react with at least one type of the chemical functional groups of the molecules on the surface of the first piece of the first element and/or the second element;
e) placing the hydrogel layer between the first element and the second element; and
f) allowing at least one type of the chemical functional groups of the molecules on the surface(s) of the first piece of the first element and/or the second element to covalently react with at least one type of the chemical functional groups of the hydrogel layer.

In yet another embodiment of the invention, said method for producing a microfluidic device according to the invention comprises the steps of
a) producing or providing the first element, a first piece of the second element, and a second piece of the second element;
b) functionalizing a surface of the first element, such as PDMS, with molecules comprising one or more types of chemical functional groups;
c) optionally functionalizing a surface of the first piece of the second element, such as PDMS, with molecules comprising one or more types of chemical functional groups;
d) producing or providing a hydrogel layer containing one or more types of chemical functional groups effective to react with at least one type of the chemical functional groups of the molecules on the surface of the first element and/or the first piece of the second element;
e) placing the hydrogel layer between the first element and the second element; and
f) allowing at least one type of the chemical functional groups of the molecules on the surface(s) of the first element and/or the first piece of the second element to covalently react with at least one type of the chemical functional groups of the hydrogel layer.

In a particular embodiment, said method further comprises between said steps d) and e) the steps of:
i) producing or providing at least one type of cell adhesion molecules, in particular cell adhesion proteins;
ii) optionally allowing at least one type of cell adhesion molecules to covalently bind to at least one type of the chemical functional groups of the hydrogel layer during the step of producing said hydrogel layer in such a way that at least one type of cell adhesion molecules is present in the bulk of the hydrogel layer;
iii) optionally seeding cells in the bulk of the hydrogel layer during the step of producing said hydrogel layer; and after said step f), the steps of:
g) covalently binding at least one type of cell adhesion molecules and at least one type of the chemical functional groups of the hydrogel layer in such a way that at least one type of cell adhesion molecules is present on the first face, the second face, or both faces of the hydrogel layer; and
h) seeding identical or different types of cells on the first face, the second face, or both faces of said hydrogel layer.

The term "functionalization" refers to attachment of molecules, chemical compounds or atoms on the surface of a material by formation of covalent bonds.

As used herein, the term "functionalizing" refers to a process of modifying surface properties of a material, for example by adding new functions via attachment of molecules, or substitution of a chemical bond by a functional group.

In an embodiment of the invention, the surface(s) of the first element, the second element or both elements is/are treated with oxygen plasma. In another embodiment, the surface(s) of the first piece and/or the second piece of the first element or the first piece and/or the second piece of the second element is/are treated with oxygen plasma. The oxygen plasma is performed in order to introduce polar surface groups, for example silanol group (SiOH). The oxygen plasma treatment "activates" the treated surface(s) by modifying said treated surface(s) to improve the surface adhesion properties. The person skilled in the art will be able to determine the parameters and conditions appropriate for the oxygen plasma treatment in order to modify a given material. As an example, a surface of PDMS may be modified by an exposure to oxygen plasma at 35 mbars, 50 mW, for 1 min.

In a particular embodiment, the oxygen plasma treated surface(s) of the first element, the second element or both elements is/are further contacted with molecules comprising thiol or sulfhydryl functional groups. This step concerns grafting or attachment of said molecules onto said oxygen plasma treated surface(s). The molecules may be comprised in a solution with a concentration in a range of 0.1 to 10% (v/v).

The molecules may have general chemical formula, $X(CH_2)n SiY_3$, which contains reactive functional groups X and Y. The X is the functional group, for example mercapto group, that is exposed on the surface of the first element, the second element or both elements, which is capable of undergoing chemical reaction, in particular with a functional group, such as vinylsulfone group, of the hydrogel layer to form covalent bonding; the n is an integer of 1 to 3; and the Y is a functional group such as methoxy, ethoxy, and methyl. The Y is the group that binds to the surface of the first element or the second element. Examples of such molecules include, but not limited to, (3-Mercaptopropyl)trimethoxysilane, (3-Mercaptopropyl)triethoxysilane, and (3-Mercaptopropyl)methyldimethoxysilane. In a particular embodiment, said molecules comprise or consist of (3-Mercaptopropyl) trimethoxysilane (MPS).

The techniques that can be used to bring the molecules in contact with said oxygen plasma treated surface(s) of the first element, the second element or both elements include(s), but not limited to, immersion (i.e. solution bath), drop casting, spin coating, dip coating, vapour deposition, etc.

In a particular embodiment, the oxygen plasma treated surface(s) of the first element, the second element or both elements is/are immersed in a solution of 1% (v/v) (3-Mercaptopropyl) trimethoxysilane (MPS) in a mixture of ethanol and acetic acid for one hour. MPS treated surfaces are then washed with 70% (v/v) ethanol and baked at 110° C. for 1H.

In a particular embodiment, the functionalized surface(s) of the first element, the second element or both elements is/are incubated in a 10 mM dithiothreitol (DTT) solution. This step ensures reduced disulphide bonds at said functionalized surface(s). Said surfaces are then rinsed with pure water and dried with compressed air.

In a preferred embodiment, the hydrogel layer is produced by crosslinking vinylsulfone functionalized polyethylene glycol (PEG-VS) macromonomers and thiol functionalized polyethylene glycol (PEG-SH) macromonomers. Said crosslinking is initiated by mixing stock solutions of said PEG macromonomers (PEG-VS and PEG-SH) using a predetermined stoichiometric ratio suitable for the preparation, for example, vinylsulfones may be added with a molar excess of 1.2 mM compared to thiols. The resulting gel-like mixture is then transferred to an appropriate support material and contacted with a flat hydrophobic material, for example a hydrophobic glass slide. Once a desired degree of polymerization or crosslinking is achieved, for example by a Michael type addition reaction between the vinylsulfone groups and the thiol groups, the resulting hydrogel is then cured at room temperature. The polymerization or crosslinking duration depends on the PEG concentration. Prior to the completion of gelation, the hydrogel is transferred to the first or second element (e.g. surface activated PDMS body) to cover one or more grooves comprised therein so that one or more microchannels are created.

In another embodiment, the PEG macromonomers, including PEG-VS macromonomers and/or PEG-SH macromonomers, are crosslinked via polypeptides to produce the hydrogel layer. Said hydrogel layer comprising polypeptides as crosslinkers are sensitive to various proteases, including metalloproteinases (MMPs).

In a particular embodiment, at least one type of cell adhesion proteins is attached, in particular through a heterobifunctional protein crosslinking reagent, to the first face, the second face, or both faces of the hydrogel layer. Said attachment of said cell adhesion proteins may be performed via perfusion of a liquid containing said cell adhesion proteins in the microchannel(s) and/or the cavity/cavities followed by an incubation period. Said cell adhesion proteins are preferably coupled with heterobifunctional protein crosslinking reagents that react with the surface functional groups of the first face, the second face, or both faces of the hydrogel layer.

The stoichiometric ratio of said cell adhesion proteins to said heterobifunctional protein crosslinking reagent is in a range of 1:1 to 1:20.

In a particular embodiment, at least one type of cell adhesion proteins is attached, in particular through a heterobifunctional protein crosslinking reagent, to the thiol groups of PEG-SH macromonomers prior to crosslinking with PEG-VS macromonomers.

The cell adhesion proteins comprise a recombinant domain fragment of fibronectin, for example FN 9-10 fragment.

The heterobifunctional protein crosslinking reagents comprise amine-to-sulfhydryl crosslinkers, for example NHS-PEG-Maleimide crosslinkers.

In one example of the invention, the maleimide groups of NHS-PEG-Maleimide crosslinkers react with thiol (—SH) groups on the first face, the second face, or both faces of the hydrogel layer.

In a particular embodiment, cells are seeded by sequentially delivering or injecting cells suspended in a liquid to the first face or the second face the hydrogel layer, via the microchannel or the cavity, followed by an incubation period.

In a particular embodiment, cells are seeded in the bulk of hydrogel by adding said cells to the mixture of PEG-VS macromonomers and PEG-SH macromonomers attached to at least one type of cell adhesion molecules.

Said cell adhesion molecules, in particular cell adhesion proteins are advantageously modified with an Fc antibody fragment or a heterobifunctional protein crosslinking reagent. Said Fc antibody fragment is adsorbed (e.g. non-covalently attached) to the hydrogel layer containing ProteinA or ProteinG or any other molecules having an affinity for Fc fragments. Said ProteinA or ProteinG or any other molecules having an affinity for Fc fragments can be incorporated into the hydrogel layer during the steps of hydrogel synthesis (e.g. can be added to the mixture of PEG macromonomers).

Said heterobifunctional protein crosslinking reagent is attached to at least one of the functional groups of the hydrogel layer, in particular, thiol groups, via formation of covalent bonding between said heterobifunctional protein crosslinking reagent and said at least one of the functional groups of the hydrogel layer, in particular thiol groups.

In particular embodiments, the hydrogel layer comprising one or more types of chemical functional groups is contacted with the surface(s) of the first element, the second element or both elements comprising molecules which comprise one or more types of chemical functional groups prior to the completion of crosslinking of the hydrogel layer so as to initiate a chemical reaction in which at least one type of the chemical functional groups of said hydrogel layer and at least one type of the chemical functional groups of said molecules on the surface of the first element, the second element or both elements form covalent bonds.

The invention also relates to a method for actuating the hydrogel layer of the microfluidic device according to the invention, comprising:
  a) introducing a liquid or gas in at least one microchannel between the first element and the first face of the hydrogel layer;
  b) introducing a liquid or gas in at least one cavity between the second element and the second face of the hydrogel layer;
  c) flowing said liquid or gas through said at least one microchannel between the first element and the first face of the hydrogel layer;
  d) flowing said liquid or gas through said at least one cavity between the second element and the second face of the hydrogel layer; and
  e) adjusting or varying the flow rate of said liquid or the pressure of said gas in said at least one microchannel or said at least one cavity so as to create a pressure differential between said at least one microchannel and said at least one cavity, which causes the hydrogel layer to expand or retract by alternatively flexing or bending towards said at least one microchannel or said at least one cavity in two opposite directions normal to the plane of the hydrogel layer.

According to the invention, the microfluidic device may be used as an organ-on-chip device, especially one comprising human cells and mimicking physiological conditions. Accordingly, actuation of the hydrogel layer may be achieved as illustrated in the examples, in particular using the following steps and/or parameters.

In a particular embodiment, said differential fluid pressure is applied by applying different flow rates of a liquid in the microchannel (i.e. between the first element and the first face of the hydrogel layer) and a liquid in the cavity (i.e. between the second element and the second face of the hydrogel layer). In one embodiment, only the flow rate of said liquid in said microchannel is varied and the flow rate of said liquid in said cavity is kept constant or static at the atmospheric pressure.

In a particular embodiment, the flow rate of said liquid in said microchannel is in a range from 0 μl·h−1 to 10,000 μl·h−1. In a preferred embodiment, the flow rate of said liquid in said microchannel is in a range from 30 μl·h−1 to 1500 μl·h−1. In one embodiment, said flow rates is periodically altered between 30 μl·h−1 to 1500 μl·h−1, with a frequency of up to 0.2 Hz. In another embodiment, a pulsatile flow of said liquid is applied in said microchannel with a burst of 1500 μl·h−1 for 5 seconds per minute.

In a particular embodiment, a stretching of the hydrogel layer up to 25%, especially 10%, is caused, in particular by cyclically ramping up the flow rate in the microchannel from 30 μl·h−1 to 1500 μl·h−1 in 10 seconds followed by a relaxation period for 10 to 50 seconds at 30 μl·h−1. Such actuation of the hydrogel layer may be carried out over a period of several days, for example 7 days.

In a particular embodiment, said liquid in said microchannel and said liquid in said cavity are identical or different.

EXAMPLES

Example 1: Hydraulically Actuated Hydrogel Layers: The Proof of Concept

An early proof-of-concept was demonstrated by investigating the actuation, e.g. by expanding and retracting, of thin hydrogel layers by means of hydraulic pressure. Practically, microfluidic devices incorporating Hydraulically Actuated Hydrogel Layers (HAHL) were made of silicon rubber (PDMS) and PEG hydrogel. Microfabrication and soft lithography were used to produce a microfluidic channel in PDMS. In a second step, thin layers of PEG hydrogel with varying elastic moduli were produced and covalently bound to the PDMS body by means of surface functionalization (mercaptopropylsilatrane). This critical step relied on the grafting of thiol groups to the surface of PDMS that were later used to covalently bind the vinylsulfone groups of the PEG hydrogel in order to create a microfluidic channel lined with one side made of a soft synthetic material equivalent to the Extracellular Matrix. This assembly allowed the seeded cells to be exposed to biomechanical and biochemical cues mimicking their native microenvironment. Finally, the PDMS/hydrogel assembly was mounted against a glass coverslip in a custom-made holder. This way, the assembled device formed a hydrogel interface that can be perfused and seeded with cells on both the upper and the lower faces.

Figure 1B:
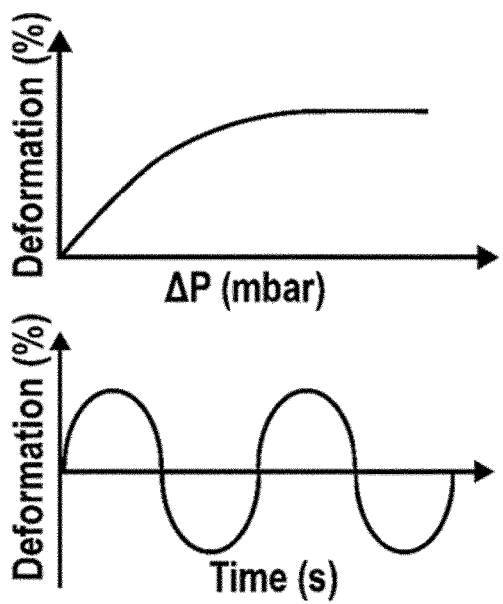

Preliminary characterization of the HAHL-based microfluidic devices demonstrated that the concept is robust enough to obtain a decent yield of device production in a reasonably equipped biomedical lab. Preliminary investigations started by verifying the hydraulic actuation of the PEG hydrogel thin layer. The cell-cultured PEG hydrogel layer could efficiently be actuated by modulating the pressure in the two microfluidic channels with the hydrogel layer interposed in-between. Furthermore, the mathematical function linking flow/pressure in the upper channel with the degree of mechanical deformation of the hydrogel layer was identified (FIG. 1A-B, D-F). With the current channel geometry and hydrogel mechanical properties, it was verified that the obtained cell stretching mimics very closely the in vivo physical landscape of the gut microenvironment (10% stretching, 0.2 Hz frequency at 5 kPa elastic modulus).

In a second step, up to three hydrogel layers could be stacked and efficiently actuated by applying hydraulic pressure in the bottom microfluidic channel. At maximum 500 μm, only 20% of the stretching amplitude was lost (dissipation). This experiment clearly shows that the HAHL based microfluidic devices can be efficiently employed for mechanically stimulating 3D cell encapsulated hydrogel layers.

Figure 1C:
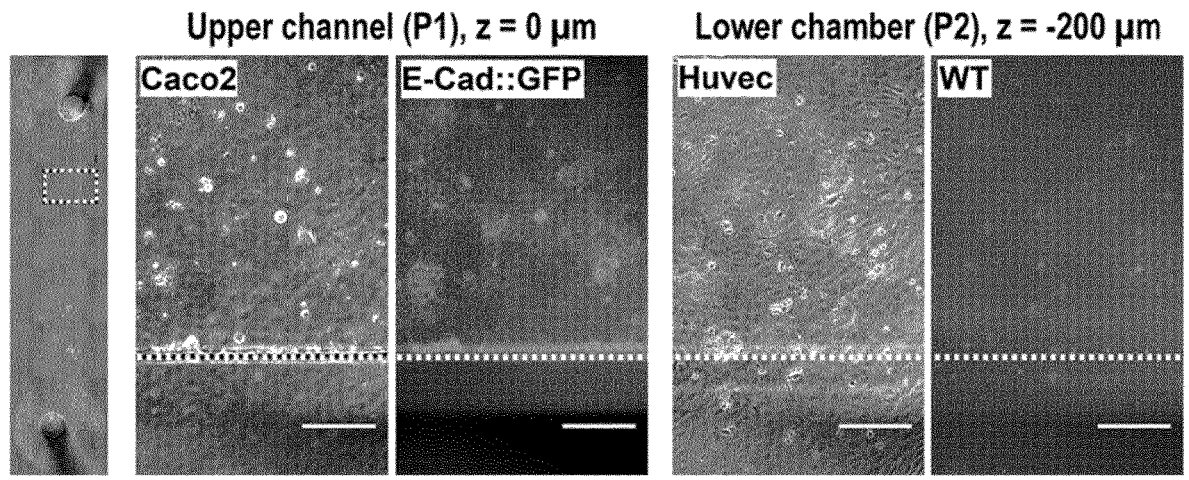
Figure 1D:
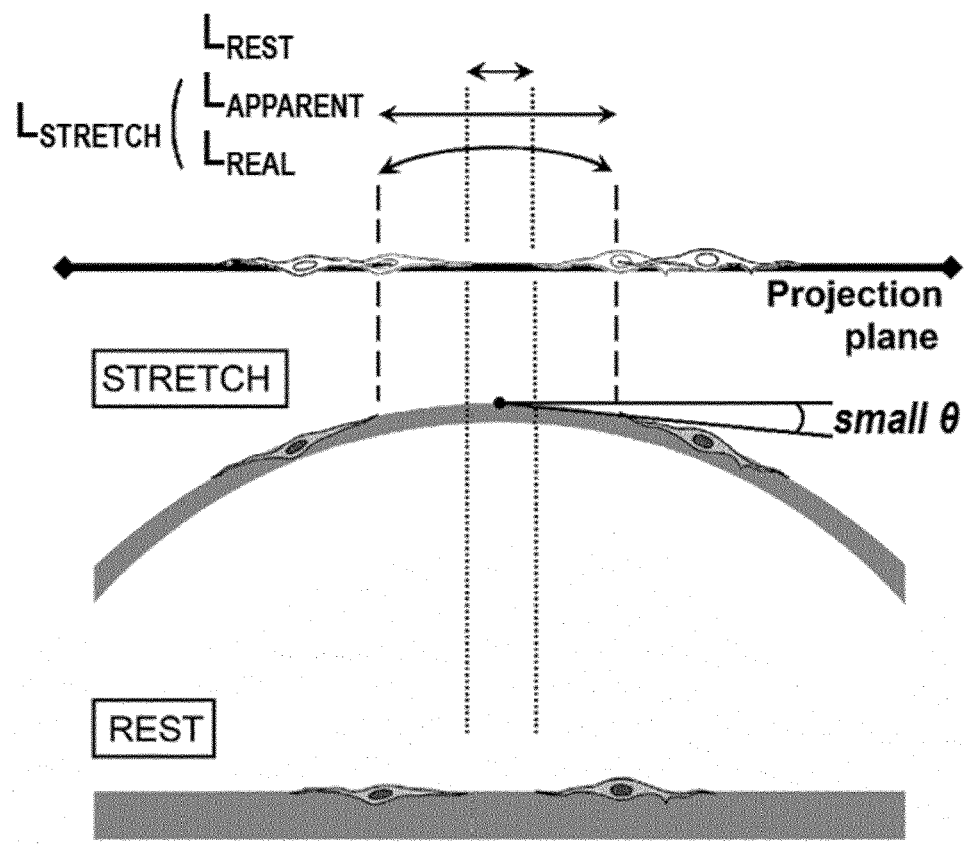
Figure 1E:
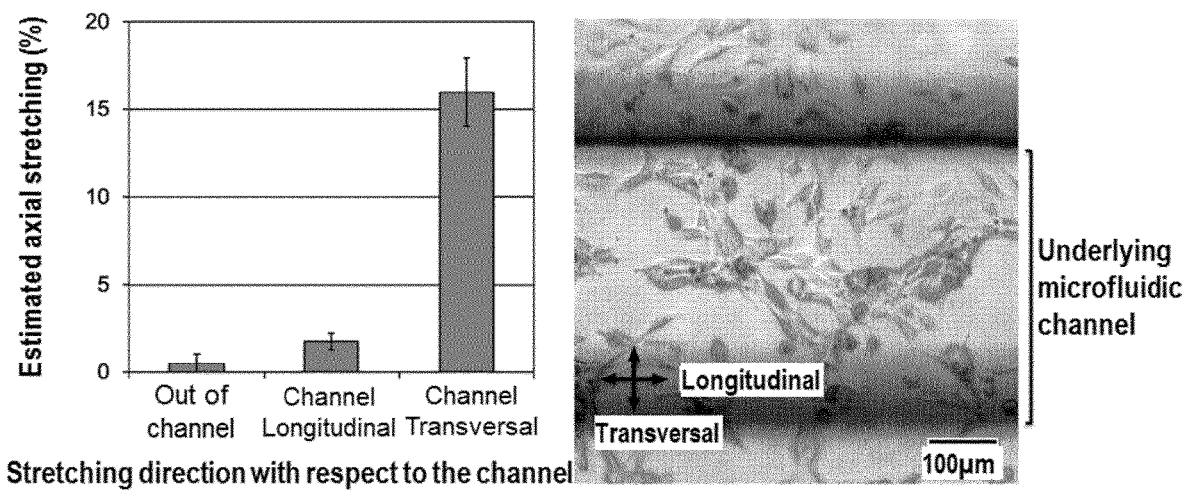
Figure 1F:
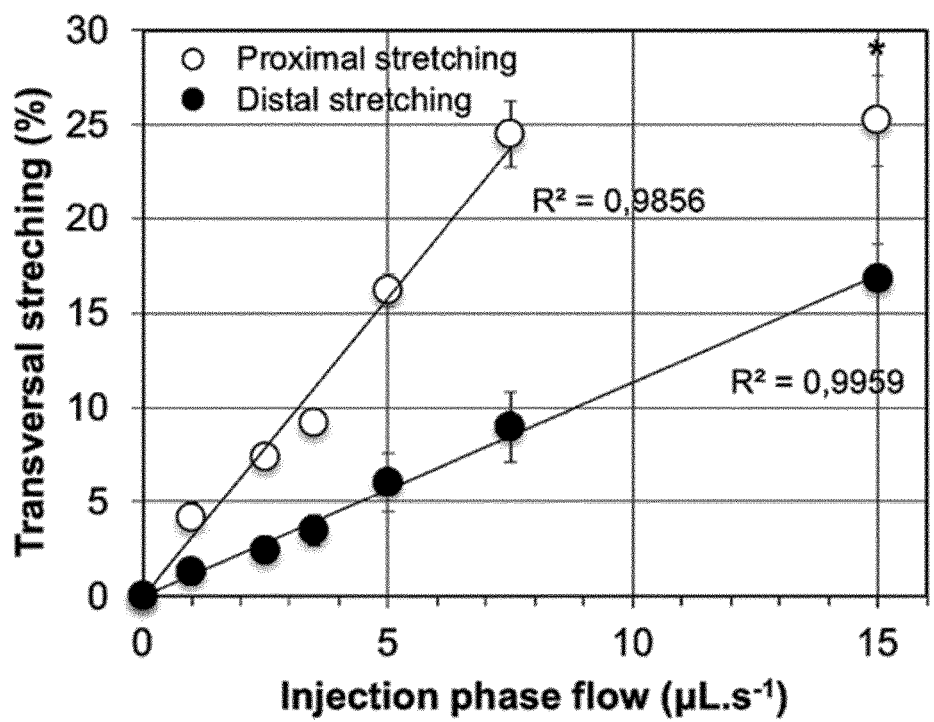

Finally, it was demonstrated that PEG hydrogels could be functionalized with fibronectin and other ECM proteins. The covalent coupling relies on Michel-type addition of the protein amines or thiols onto the vinylsulfone groups of the PEG hydrogel. This strategy was found to be efficient for promoting cell adhesion to the otherwise inert PEG material. For instance, multiple cell types were efficiently seeded on HAHL-devices including primary cells (HUVEC) or derived cell lines (fibroblasts, C2C12, Caco2 . . . ) (FIGS. 1C and E). These preliminary experiments also showed that the seeded cells adhered nicely, underwent the mechanical stimulation for up to 17 days and survived.

Example 2: Determining Optimal Hydrogel Mechanical Properties: Gel Concentration and Thickness A variety of PEG hydrogel concentrations ranging from 2.5% to 10% were tested. In all condition we preserved 1.2 mM free SH groups in order to further immobilize proteins or peptides if need be. Both 170 μm and 340 μm thick gels were also produced in order to identify the optimal condition in which gels bound to PDMS stretch but do not burst under hydraulic load. The most successful HAHL-device setup was based on 5%, 170 μm thick PEG gels. Under these conditions, it was demonstrated that 50% or more of all the produced devices did not leak and could withstand hydraulic actuation. Furthermore, it was demonstrated that HAHL-devices can be produced with hydrogels of varying PEG concentration and thus varying elastic modulus. Typically, HAHL-devices could be produced with hydrogels containing 5 to 10% (w/v) PEG that correspond to a shear modulus (G') of 10 to 30 kPa, respectively.

Example 3: Actuating the HAHL-Based Micro Fluidic Device

After securing a robust assembly protocol for the HAHL-device, the relationship between differential flow rates applied to the device and the degree of stretching of the PEG hydrogel layer was investigated. It was possible to perfuse up to 10,000 μl·h$^{-1}$ in the upper channel without bursting the hydrogel. This condition corresponded to a uniaxial stretch of approximately 20%.

Figure 2:
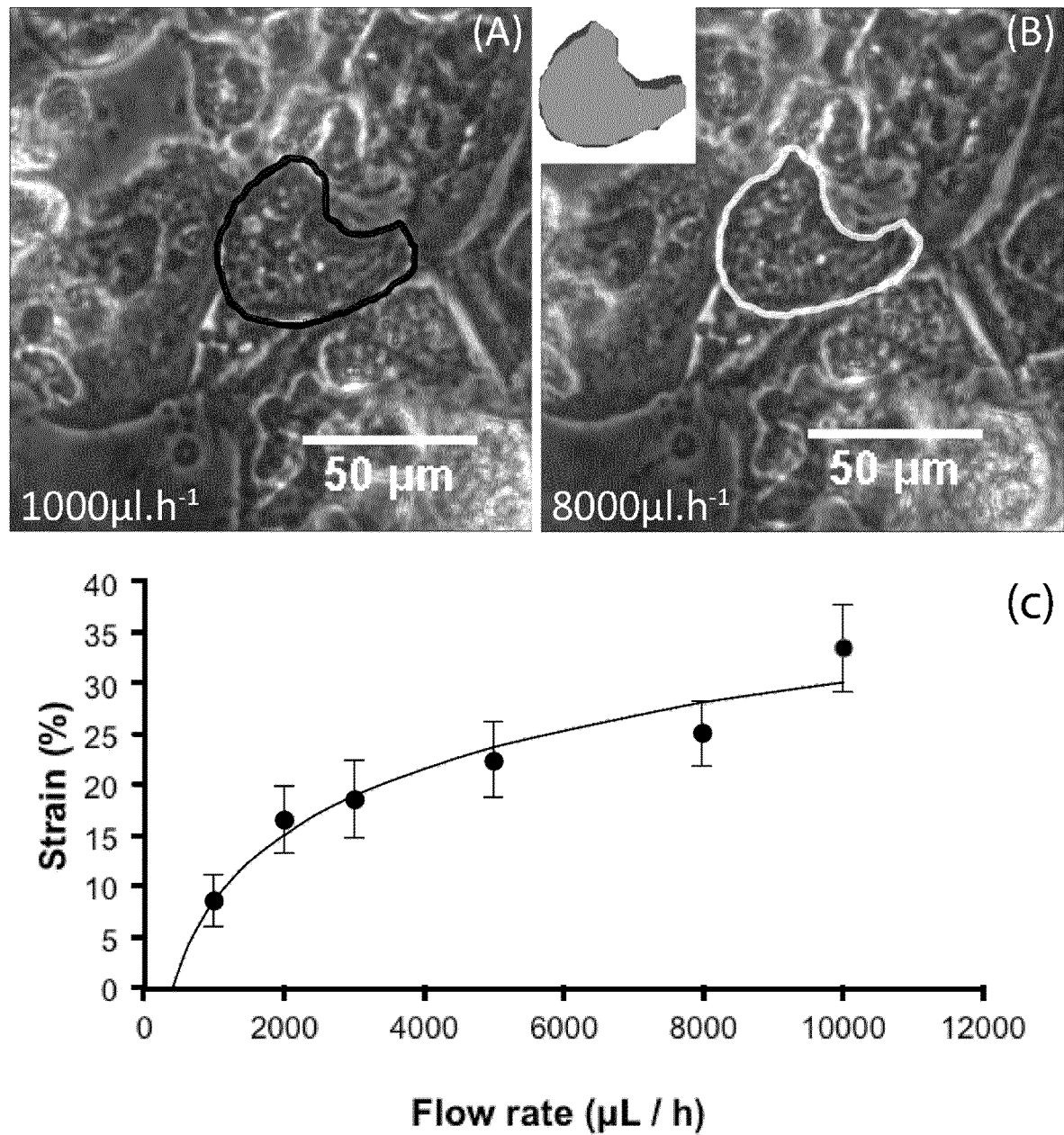
FIG. 2: Quantitative assessment of the relationship between flow rate and mean cell area deformation. A and B panels show two photographs of cells mechanically stimulated on the HAHL-device under different flow rates. The trendline was calculated as logarithmic due to the way stretching occurs in materials.

In order to confirm that the obtained hydrogel deformation affected the cells seeded on both faces of the hydrogel layer, the hydrogel layer was functionalized with a fibronectin fragment and seeded Caco2. After the cell adhesion, the HAHL devices were submitted to a range of flow rates and cell deformation was measured (FIG. 2A-B). A continuous flow rate of 30 μl·h$^{-1}$ did not yield observable deformation whereas increasing the flow rate to 1500 μl·h$^{-1}$ instantaneously increased the average cell area by 10% (FIG. 2C). Most noticeably, this actuation could be made periodically by alternating the flow rates between 30 and 1500 μl·h$^{-1}$ with a frequency of up to 0.2 Hz.

Example 4: Maturing a Gut-On-Chip in the HAHL-System

Figure 3:
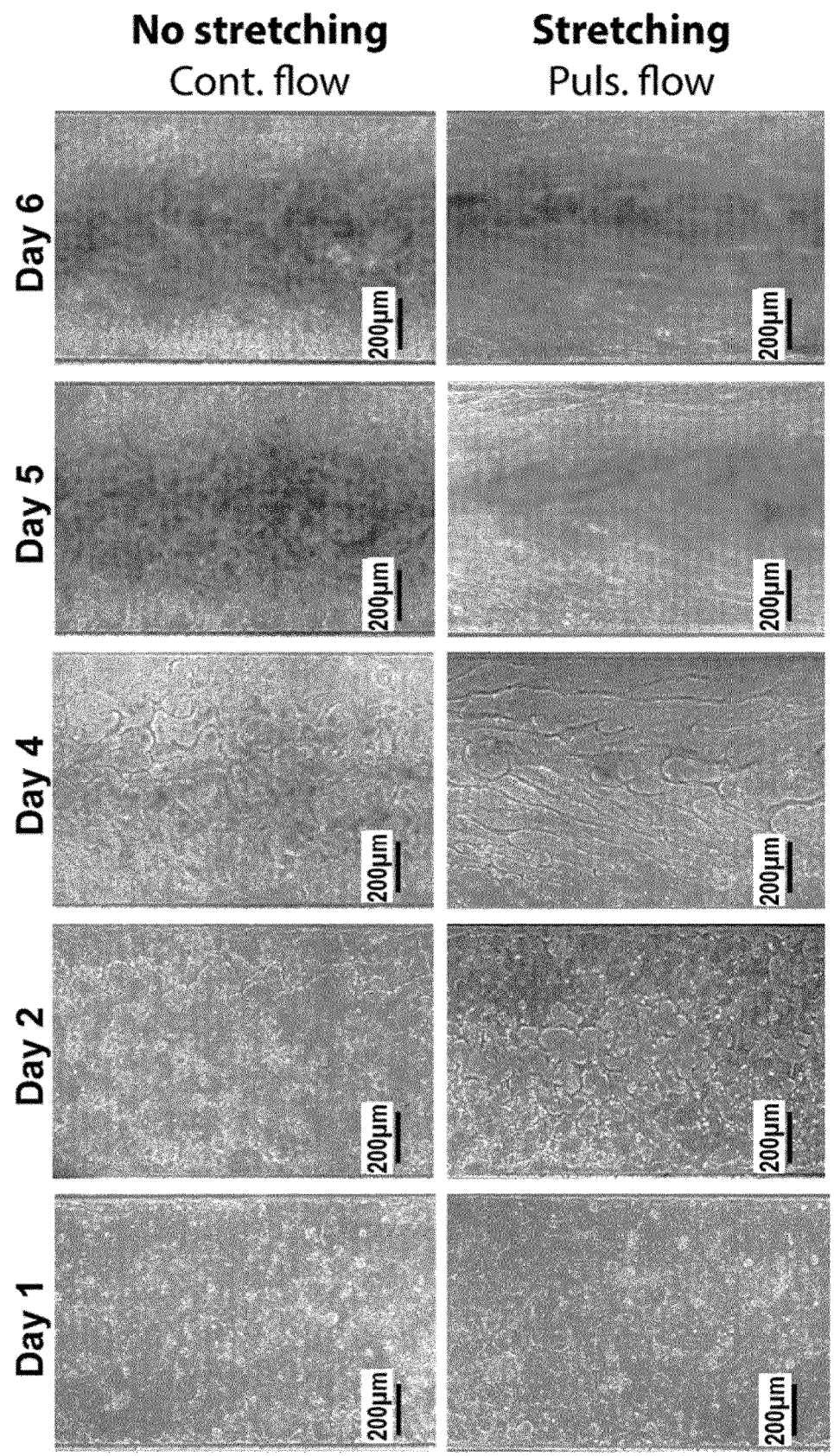
FIG. 3: Epithelial differentiation on the HAHL-microfluidic device. Seeded CaCo2 cells show clear signs of 3D organization into villi-like structures as early as 2 days after seeding (stretching conditions: under continuous flow). The same cells still undergo 3D organization with a 24 h delay.

After the completion of the mechanical characterization of the HAHL-devices, the inventor decided to investigate the maturation of the endothelial and epithelial linings (HUVEC and CaCo-2, respectively) as cultured on these devices. The two cell types where consecutively seeded and perfused with a constant flow rate of 30 µl·h$^{-1}$ on both upper and bottom channels. After a few days, flat and robust monolayers of endothelial and epithelial cells were observed and pulsatile flow (a burst of 1500 µl·h$^{-1}$ for 5 seconds per minute) was started in order to induce stretching of the hydrogel and the cells. Clear and distinctive signs of differentiation were observed on both epithelial and endothelial sides of the device. FIG. 3 shows that CaCo-2 monolayers started organizing in 3D as early as two days after the beginning of the hydraulic actuation. Structures reminiscent of the large intestine's villi were observed. On the endothelial side, HUVEC organization changed from continuous monolayer to a branched/tubular network (FIG. 3). When static versus actuated HAHL-devices were compared, it was found that cyclic strain sped the emergence of 3D structures by 24 to 48 hours.

Globally, these experiments demonstrated that:
- The hydraulic actuation of thin hydrogel layers could be successfully sustained for more than seven days.
- Hydraulic actuation, as descried here, do not cause cell or hydrogel delamination
- Hydraulic actuation of the seeded cells allowed for a faster and better differentiation
- Seeded cells survived and differentiated on HAHL-devices efficiently recapitulating the structure of a healthy gut tissue.
- The HAHL system is fully compatible with continuous observation by time-lapse microscopy provided that the microscope is equipped for live imaging.

Example 5: Photolithography Masters Production

The design of HAHL-device was produced in CleWin a physical layout editor software (Phoenix software, USA). Briefly, the first layer of the design was comprised of two channels 7.5 mm long and 1 mm wide. These straight channels were connected to both inlets and outlets (2 mm diameter). The second layer was designed to provide an 18 mm diameter recess that can harbor the thin hydrogel layer which is referred herein as "pool". Corresponding photolithography masks, printed at 50000 DPI on a transparent plastic sheet, were ordered from Selba S.A (Switzerland). Micrometric alignment marks were introduced on the two masks in order to ensure that both microfluidic channels would be produced at the center of the pool. Next, a 4" diameter silicon wafer (Neyco S.A., France) was used as a substrate for photolithography. Spin-coating of SU8-2100 resin (Microchem, MA, US), soft bake, exposure and post exposure bake parameters were adjusted to obtain a thick first layer of 500 µm. Photolithography was performed on a MJB4 mask aligner (Süss). The second layer containing the microfluidic channels, was then produced with microfabrication parameters targeting a thickness of 250 µm. Finally, the microfabricated master was developed in propylene glycol monomethyl ether acetate (PGMEA, Sigma Aldrich, MI, US) and hard baked at 200° C. for 2 hours. The height of the produced structures was then measured on a Dektak XT stylus profiler (Bruker, USA).

Example 6: Soft Lithography (PDMS Body Production)

First, 30 g of polydiméthylsiloxane (PDMS, Sylgard 184 Dow Corning) base was mixed with a curing agent in a ratio of 1:10. Then the obtained solution was vigorously stirred for 3 min and degassed by keeping it under vacuum for another 30 min. The obtained mixture was poured into a petri dish containing the microfabricated mold without introducing new bubbles. Finally, the cast PDMS was baked for 2 hours at 80° C. in order to obtain a fully cross-linked replica of the microfabricated master.

Once the PDMS has cured, a scalpel and a small spatula were used to remove the PDMS from its mold. The PDMS surface containing the microfluidic channels was then covered with magic scotch tape (3M). The obtained PDMS was then punched with a 35 mm diameter puncher in order to center the microfluidic channels when placing the chips in the custom-made holder. Next, inlets and outlets were punched out using a hole puncher with an inner diameter of 0.75 mm. These connections were made with a 45-degree angle in the prolongation of the central channel in order to reduce the load on the hydrogel upon perfusion.

Example 7: Surface Functionalization of the PDMS Body

Each PDMS body was fitted with four metal connectors to ensure an easier connection to the fluidic main line. A droplet of cyanoacrylate glue was dabbed around the base of the protruding connector in order to prevent fluid leakage. Next, the scotch tape was removed and the PDMS body was placed face up in a plasma cleaner. The PDMS body was then exposed to an oxygen plasma at 35 mbars, 50 mW for 1 min. Once the surface was activated, the PDMS body was immersed in a solution of 1% (v/v) 3-mercaptopropyl-(trimethoxy)-silane (MPS) in absolute ethanol (300 ml) plus 10 drops of acetic acid for one hour (all the chemicals were purchased from Sigma Aldrich). This was followed by two 70% ethanol washes and the PDMS body was air-dried on a non-fibrous tissue for 10 minutes before being placed into an oven at 110° C. for one hour. The PDMS body was then stored at 4° C.

Example 8: Hydrogel Casting and Bonding to the Surface of PDMS Body

Prior to the preparation of hydrogel, the PDMS body was first incubated in a 10 mM dithiothreitol (DTT) solution for a minimum of 10 minutes in order to reduce the disulphide bonds at the surface of the PDMS body. Hydrogels were prepared by mixing stock solutions of two different functionalized polyethylene glycol (PEG) macromonomers of 10 kDa (NOF corporation, Japan). Four-arm thiol- and eight-arm vinylsulfone-functionalized PEG macromeres were mixed using a stoichiometric ratio insuring an excess of 1.2 mM of vinylsulfone. Typically, 50 µl of 7.5% (w/v) PEG hydrogels were obtained by mixing 10.1 µl of PEG-VS (12% w/v), 21.2 µl of PEG-SH (12% w/v) and 18.7 µl of triethanolamine (TEA) buffer (0.3 M, pH 7.5). While still liquid, 40 µl of the gelling mixture was pipetted onto a Teflon cylinder containing a single well (18 mm diameter, 260 µm deep) and covered with a hydrophobic glass slide (SL2, Sigma Aldrich). Polymerization of the hydrogel was achieved by a Michael-type addition reaction of the vinylsulfone functions onto the thiol groups. Crosslinking time duration was varied across all tested PEG concentration; typically, 7.5% PEG gels were left for 30 min at room temperature in order to cure. Three minutes before gelation or completion of cross-linking, the PDMS body left in DTT were thoroughly rinsed with milli-Q water and dried with filtered compressed air. Then, the hydrophobic glass slides were carefully removed from the Teflon molds containing the gels. An activated PDMS body was then gently pressed onto the surface of the hydrogel so that the hydrogel covers completely the two channels of the PDMS body. When covering the hydrogel, the sides of the PDMS body were gently pressed so that the inner center touches the hydrogel homogenously, forcing out any air bubbles. At this step, it was important to ensure that the hydrogel is flat so that the channels are evenly covered by the hydrogel, and that the PDMS surface within the channels does not touch the hydrogel. The assembly was then left for one hour at room temperature in order for the excess vinylsulfone groups of the hydrogel and the thiols of the PDMS surface to covalently react. Once bonded, the two pieces were carefully separated, with the hydrogel transferred to the surface of the PDMS body.

Example 9: Recombinant Protein Production and PEGylation

In order to seed cells on the HAHL-device, the otherwise inert PEG hydrogel needs to be rendered cell-adherent. A recombinant fibronectin domain 9 and 10 domain was used to promote cell adhesion. The corresponding synthetic gene was ordered from Eurofins™ (France). Cloning in pGEX-4T-1 expression vector (GE Lifesciences), expression and purification was performed at the Platform of recombinant proteins at Institut Pasteur. The FN9-10 fragment was expressed in *E. coli* BL21 Star™ (DE3) in 4L cultures. Purification of the recombinant protein was performed on GST columns followed by a thrombin cleavage of the purification tag. Purified FN9-10 fragment was concentrated at 3.5 mg·ml$^{-1}$ in PBS. the resultant FN9-10 fragment was then coupled, via its free secondary amines, to a 3.5 kDa heterofunctional NHS-PEG-Maleimide linker (NOF Corporation) with a stoichiometric ratio of 1:4. Incubation was carried out for 1 hour at room temperature 500 µl of FN9-10 at 3.5 mg·ml$^{-1}$ with 29 µl PEG linker at 50 mg·ml$^{-1}$. PEGylated FN9-10 solution was then perfused in the microfluidic channel and on the free surface of the hydrogel. Treated HAHL-device was then incubated for 2 hours at 37° C. Finally, the excess of FN9-10 was washed away with a PBS wash.

Example 10: Cell Seeding

HAHL-device can be seeded with a variety of different adherent cells. Both TC7 CaCo2 epithelial cells and HUVECs (Human umbilical vein endothelial cells) were used in this example. Prior to seeding on the HAHL-device, the cells were cultured on regular T75 flasks. The cells were then harvested by trypsinization. Three ml of trypsin (0.05% for HUVECs and 0.25% for CaCo cells) was pipetted onto the cells. After 5 minutes at 37° C., the flask was inspected under a microscope to check for cell detachment. Six ml of medium was added and the detached cells were collected in a 50 ml tube. The cells were then centrifuged at 300 g for 5 minutes and the supernatant was discarded. The pellet was resuspended in 300 µl of medium. Cell concentration was assessed by pipetting 20 µl onto a Malassez hemocytometer. The concentration was adjusted to 1 million cells·ml$^{-1}$ for HUVECs, and to 6-8 million cells·ml$^{-1}$ for Caco2. The seeding procedure started by delivering 100 µl of HUVECs suspension on the hydrogel part of inverted HAHL-device. Upon incubation (30 min at 37° C.), HUVEC adhered nicely to the fibronectin coated hydrogel. A PBS wash was performed to remove non-adherent cells. The seeded HAHL-device was then flipped and the Caco2 cell suspension was injected into the microfluidic channel. Again, the HAHL-Chips were placed at 37° C. overnight in order to ensure a good adhesion of the Caco2 cells. The excess of non-adherent Caco2 cells was then remove by gently perfusing medium in the microfluidic channel. Cell culture in these static conditions (no perfusion) continued for another 24 hrs in order to obtain a confluent monolayer of both HUVEC and Caco2 cells.

Example 11: HAHL-Device Assembly

Before seeding the cells, The HAHL-device was assembled in a custom made holder. First, a round 30 mm-diameter coverslip was placed in the holder. Second, a PDMS ring (35 mm OD, 20 mm ID, 1 mm thickness) was placed on top of the coverslip forming a small reservoir. Before placing the HAHL device the reservoir was filled with EGM2 medium (Lonza) while ensuring no air bubbles were trapped. The HAHL-device was then placed with the hydrogel facing the reservoir. Finally, the assembly was closed hermetically by screwing-in the tightening ring. The insertion of Tygon™ tubing (pre-filed with PBS) in the fluidic connectors of the chip ensured a proper microfluidic interface.

Example 12: HAHL-device Perfusion

Once a monolayer was obtained, the upper microfluidic channel of the HAHL-device was connected, via Tygon tubing, to a Hamilton glass syringe containing Caco2 medium. Continuous perfusion at 30 µl·h$^{-1}$ was started by connecting the syringe to a neMESYS pump system (Cetoni GmbH). The actuation protocol for the HAHL-device was varied in order to investigate different stretching regimes. Typically, a 10% stretching of the hydrogel layer was obtained by cyclically ramping the flow rate from 30 to 1500 µl·h$^{-1}$ in 10 seconds followed by a relaxation period (10 to 50 seconds at 30 µl·h$^{-1}$). Both flow rates and periods were adjusted to vary the strain on the hydrogel layer. Each experiment was typically carried out over a period of 7 days. The control of the flow rate profiles over time was automated by developing corresponding scripts in the Qmix software (Cetoni GmbH).

Example 13: HAHL-Device Live and Fixed Imaging

Image acquisition protocol was varied extensively to fit the needs of each experiment. Snapshots, time-lapse, mosaics and z-stacks were all acquired on an Axio Observer Z1 inverted motorized microscope (Carl Zeiss, Germany) equipped with epifluorescence (Collibri™ 2), incubation chamber and Orcaflash V4.0 CMOS camera. Most images were acquired with a 10×, 0.45 NA, phase1 objective.

After cell culture for varying periods of time, HAHL-device was fixed for later staining and imaging. First, two washes were carried out by immersing disassembled device 5 min in phosphate-buffered saline (PBS) solution (ThermoFischer scientific). Then, the device was submerged in 4% (w/v), pH 7.4 paraformaldehyde (Sigma Aldrich, MI, US) solution for 15 minutes. Final two PBS washes were carried out before the device was sealed in a petri dish and kept at 4° C.

Example 14: Cell Stretch Quantification

Before the experiment began, one device was selected (one day after seeding) for cell stretch quantification. The device was perfused with a pressure from 20 mbar up to 70 mbar with an increment of 10 mbar. The CaCo-2 cells were imaged at each pressure increment and the image analysis software "Fiji" was used to quantify the stretch. Five cells were selected from an imaged section and a region of interest was drawn around them at each pressure increment. The area of the cell was measured and compared at each pressure increment. The difference in area was calculated and a stretch in percentage was noted at each pressure increment, averaged over the 5 cells. The stretching of the cell was then converted to a flow rate using an established relationship specific to the HAHL-device. The need for many repeats means that one device must be selected from each experiment to narrow the error margin and increase accuracy.

Exemplary Embodiment of a 3D Configuration of the Microfluidic Device

Figure 4A:
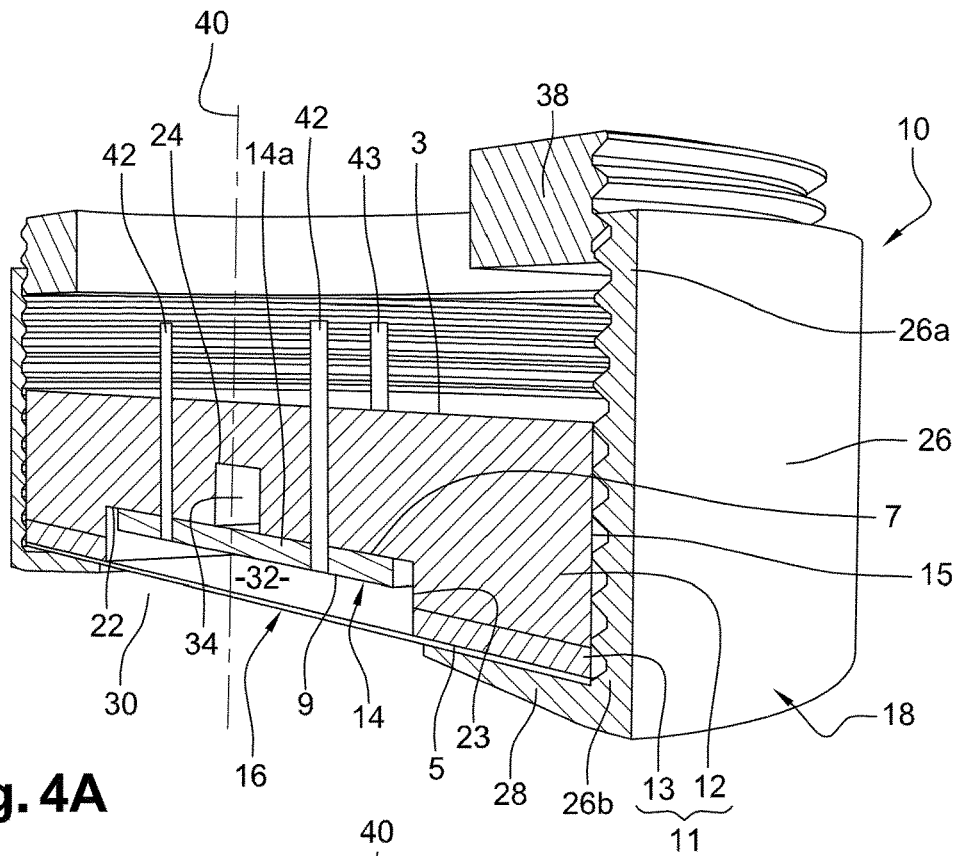
FIG. 4A: A three-dimensional cross-sectional view of a microfluidic device according to the invention according to a plane passing through a microchannel and a cavity.
Figure 4B:
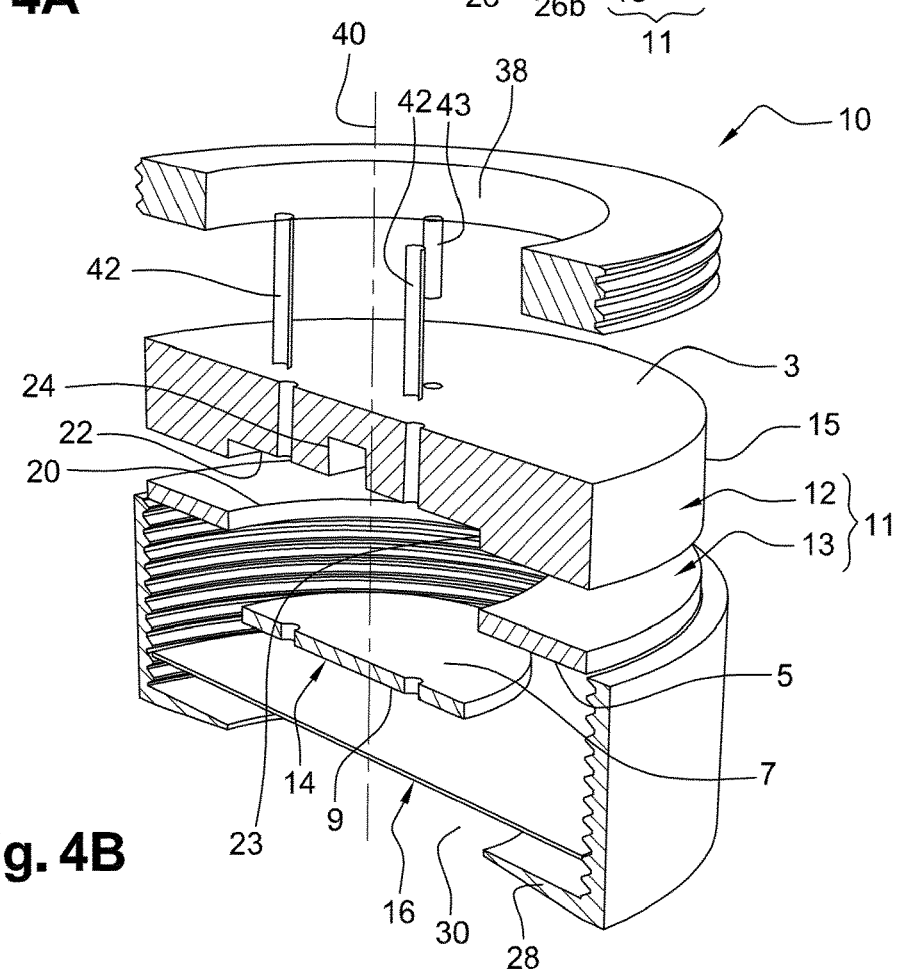
FIG. 4B: An exploded view of the constituent elements of the device shown in FIG. 4A.

We now refer simultaneously to FIG. 4A and FIG. 4B that represent a microfluidic device 10 according to an embodiment of the invention. The microfluidic device 10 is formed of several parts that are assembled together to form the microfluidic device 10. Then, it comprises a first element 11, a hydrogel layer 14 and a second element 16. These three parts 11, 14, 16 are mounted inside a holder 18. The first element 11 is formed of one first piece 12 and one second piece 13 that are separate.

In the embodiment disclosed in the figures, the microfluidic device 10 has a general cylindrical shape. However, it is understood that the device 10 may have any other shape.

Figure 5:
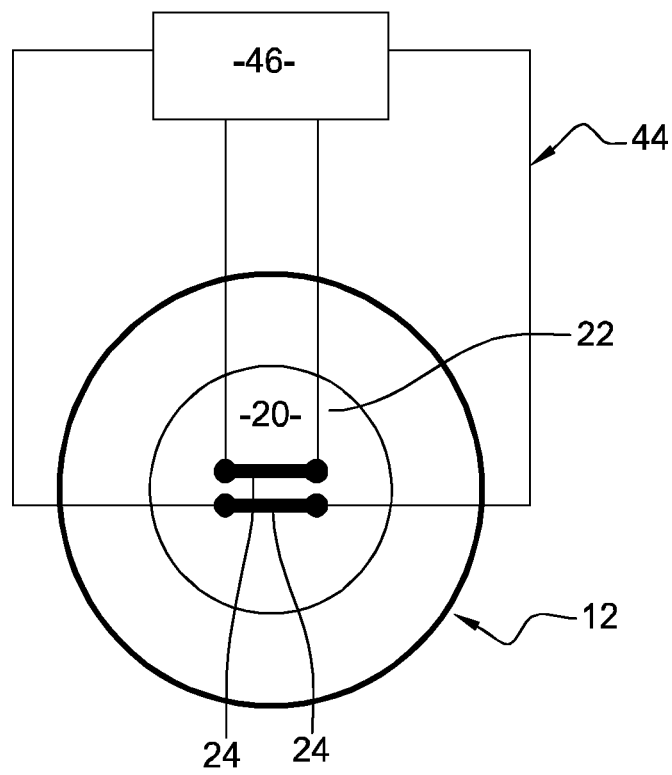
FIG. 5: A sectional view of an exemplary embodiment of a first element of a microfluidic device according to the invention.

More specifically, the first piece 12 may be made of any transparent material onto which thiol groups can be grafted. The first piece 12 has a thickness ranging from 2 to 25 mm. The first element 11 has a first surface 3 and a second surface 5 opposite to each other along a direction 40 substantially perpendicular to the first element 11. The first 3 and second 5 surfaces are joined together by a peripheral surface 15 that may be cylindrical. A recess 20 is formed on the first element 11 so as to open out on the second surface 5 when the microfluidic device is assembled as represented in FIG. 4A. In particular, the recess 20 is formed partially within the first piece 12 and by the second piece 13. The recess 20 comprises a bottom surface 22 and a cylindrical side wall 23 forming the outer boundary. At least one groove 24 is formed on the bottom of the recess, for example two as shown in FIG. 5. In an exemplary embodiment, the groove 24 is straight and may have a width ranging from 0.1 mm to 5 mm and depth ranging from 0.1 mm to 5 mm, the length being comprised between 0.2 mm and 20 mm. The groove 24 or grooves may be formed using any kind of technologies, such as photolithography. In an embodiment, it is understood that the second surface 5 may be substantially annular due to the general cylindrical shape of the first element 11.

The recess may have a different shape than the one described in the figures. For example, the recess may be square or rectangular. The recess may thus comprise several side walls joined together to delineate the outer boundary or perimeter of said recess.

In the exemplary embodiment represented in the figures, the second element 16 is formed by a thin flat piece of transparent material, i.e. a coverslip or coverglass, which may have a constant thickness ranging between 0.1 mm and 0.17 mm.

As shown in FIGS. 4A and 4B, said first element 11 formed by the first piece 12 and the second piece 13, said second element 16 and said hydrogel layer 14 are mounted within the holder 18 comprising a cylindrical wall 26 having a first end 26a and a second end 26b, the second end 26b being connected to an annular radial wall 28 forming an abutment wall for the mounting of the second element 16. As shown, the radially inner end of the annular radial wall 28 delineates an opening 30. The second element 16 covers the exit of the recess 20 and therefore delineates with the hydrogel layer 14 and the cylindrical wall 23 of the recess 20 a cavity 32.

The hydrogel layer 14 comprises a first face 7 oriented towards the bottom face 22 of the recess 20 and a second face 9 opposite to the first face 7 and oriented towards the second element 16. The first face 7 of the hydrogel layer 14 is applied onto the bottom face 22 of the recess 20 so as to close said groove or grooves in order to form a microchannel 34 or microchannels.

The microfluidic device 10 is assembled in the following manner. The hydrogel layer 14 is mounted inside the recess 20, the dimensions and shape of which are so as to completely house the hydrogel layer 14 therewithin. More specifically, in this embodiment, the dimensions and shape of the recess are configured so as to allow the hydrogel to completely fit within the recess without having to deform (e.g. wrinkle or fold) the hydrogel layer. The side wall(s) of the recess surround(s) the periphery or edge of the hydrogel layer with or without being in contact therewith.

The hydrogel layer 14 covers said groove 24 or grooves formed on the bottom surface 22 of the recess 20 so as to form microchannels 34. The second element 16 or coverslip is mounted inside the holder 18 and in abutment with the radial wall 28, and the assembly formed by the first element 11 and the hydrogel layer 14 is mounted inside the holder 18 so that the second annular surface 5 is pressed against the second element 16 or coverslip. We note that second piece 13 of the first element 11, has an annular shape, and for example a rectangular section. The second piece 13 is interposed between the second element 16 and the first element 11 so as to perfectly seal the junction of the first piece 12 of the first element 11 and the second element 16. A clamping element 38 is mounted on the holder 18 and allows assembling of the device by tightening of the first element 11 and second element 16 onto the radial wall 28 of the holder 18. The clamping element 38 here is formed by a nut screwed on the threaded inner surface of the cylindrical wall 26 of the holder 18.

As clearly represented in the FIG. 4A, the hydrogel layer 14 is interposed between the first element 11 and the second element 16 in a given axis 40 that is substantially perpendicular to the hydrogel layer 14. Moreover, the shapes and dimensions of the first element 11, the second element 16 and the hydrogel layer 14 are determined to delineate at least one microchannel 34 between the first element 11 and the first face 7 of the hydrogel layer 14 and at least one cavity 32 between the second element 16 and the second face 9 of the hydrogel layer 14, said at least one microchannel 34 and said at least one cavity 32 being arranged relative to each other so that said given axis 40 intercepts both said at least one microchannel 34 and said at least one cavity 32.

To allow the introduction of liquid within the cavity 32, conduits 42 pass through the first element 11 and more precisely through the first piece 12 of the first element 11 and the hydrogel layer 14, at least one conduit 42 being for introduction of liquid and at least one other conduit 42 being for withdrawing liquid. Also, FIG. 4B exhibit one conduit 43 for the introduction of liquid or gas within the microchannel 34 defined by the groove 24 and the hydrogel layer. Obviously, the microfluidic device further comprises a conduit (not shown) for the withdrawing of the fluid.

It is also noted that the first element 11 may comprise only the first piece 12, i.e. without the second piece 13.

The microchannels 34 are connected to a circuit 44 (FIG. 5) of fluid that comprises means 46 (FIG. 5) for varying the differential fluid pressure between said at least one microchannel 34 and said at least one cavities 32. The connection of the at least one microchannel 34 with said means 46 for varying the differential pressure and the arrangement of the cavity 32 and microchannels 34 as mentioned above in a given axis, allows the hydrogel layer 14 to expand or retract by alternatively flexing or bending towards said at least one microchannel 34 or said at least one cavity 32 in two opposite directions normal to the plane of the hydrogel layer.

In the most effective embodiment, the microchannel 34 measured 8 mm in length. It was 1 mm wide and 0.250 mm deep. Cavity 32 had a diameter of 20 mm and was 2 mm deep.

It should be considered that the term "element" used to refer to the "first element" or the "second element" may designate an element that is a one-piece construction, i.e. manufactured as a single piece. It may also designate an element that comprises several independent pieces as it will be described in the following description of FIG. 6 and it is the case in the embodiment of FIG. 4A.

It should be clearly understood that the first element and the second element are separate pieces that are assembled together to define a housing within which the hydrogel layer is mounted. According to this interpretation, each of the recess, the cavity and the at least one grooves are comprised within the housing. The first element and the second element are in contact so as to define a closed sealed contour at the junction between the first element and the second element.

Also, in all the embodiments, the hydrogel layer does not experience any pressure exerted by any of the first element or the second element and as a consequence of any sub-piece of the first and second elements.

Figure 6:
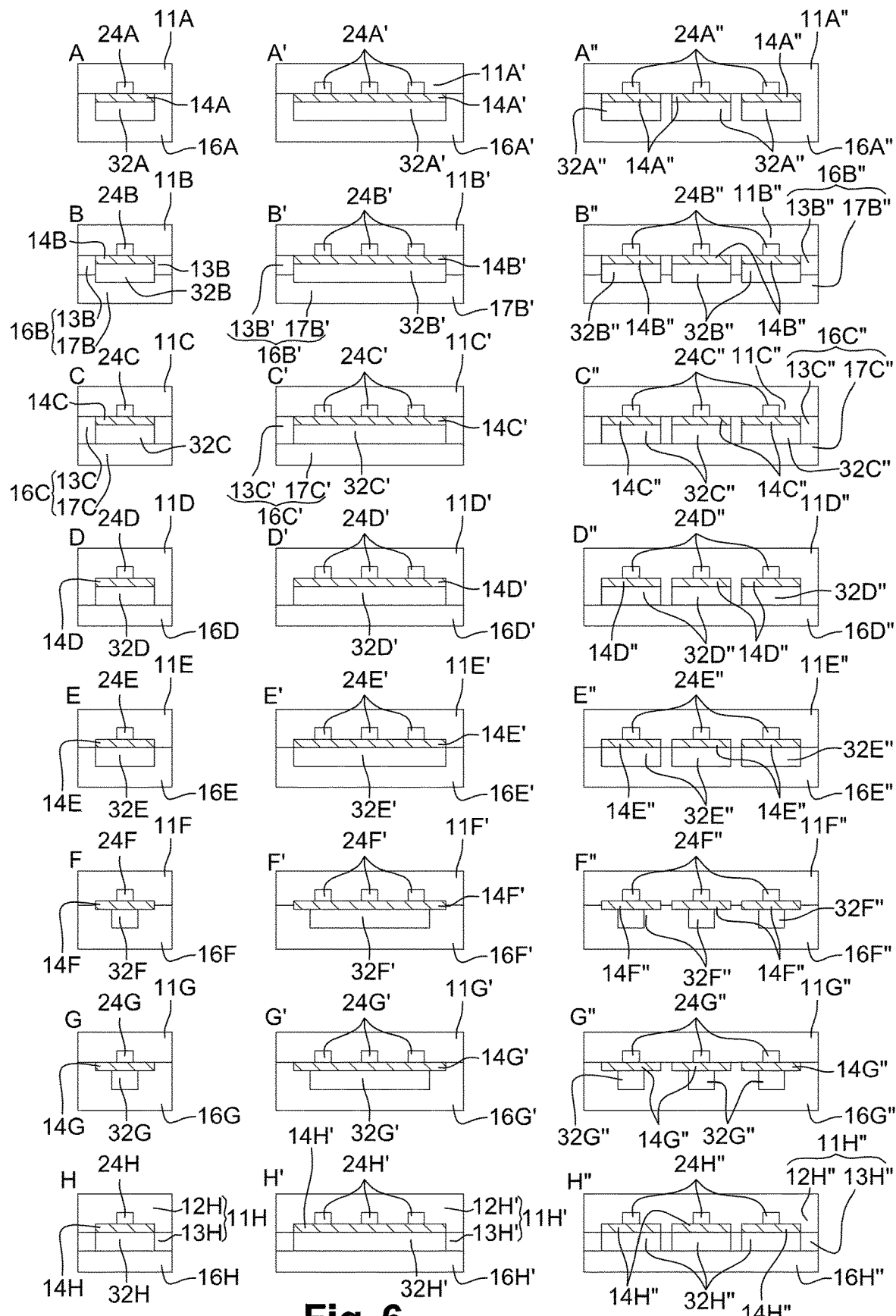
FIG. 6: Various device configurations (cross-sectional view) according to the invention.

Indeed, we will now refer to FIG. 6 that represents different configurations of a microfluidic device of the invention within which the first and second elements have different shapes. Even if not described, the microfluidic devices, that are hereafter described, comprise each a circuit of fluid that may comprise differential fluid pressure means as described in reference to FIG. 5.

In the different embodiments of FIG. 6 described hereafter:

the first column corresponds to FIGS. 6A to 6H that represent one schematic illustration of one microfluidic device comprising a first element 11A, 11B, 11C, 11D, 11E, 11F, 11G, 11H with one groove 24A, 24B, 24C, 24D, 24E, 24F, 24G, 24H, one hydrogel layer 14A, 14B, 14C, 14D, 14E, 14F, 14G, 14H and a second element 16A, 16B, 16C, 16D, 16E, 16F, 16G, 16H, the hydrogel layer defining a cavity 32A, 32B, 32C, 32D, 32E, 32F, 32G, 32H with the second element;

the second column corresponds to FIGS. 6A' to 6H' that represent one schematic illustration of the same arrangement as shown in respective FIGS. 6A to 6H but with the hydrogel layer 14A', 14B', 14C', 14D', 14E', 14F', 14G', 14H' covering simultaneously several grooves 24A', 24B', 24C', 24D', 24E', 24F', 24G', 24H' formed within a same first element 11A', 116', 11C', 11D', 11E', 11F', 11G', 11H 'and defining one single cavity 32A', 32B', 32C', 32D', 32E', 32F', 32G', 32H' with the second element 16A', 16B', 16C', 16D', 16E', 16F', 16G', 16H'; and the third column corresponds to FIGS. 6A" to 6H" that represent one schematic illustration of the same arrangement as shown in respective FIGS. 6A to 6H but with several hydrogel layers 14A", 14B", 14C", 14D", 14E", 14F", 14G", 14H" each covering one groove 24A", 24B", 24C", 24D", 24E", 24F", 24G", 24H" formed within a same first element 11A", 11B", 11C", 11D", 11E", 11F", 11G", 11H", each hydrogel layer 14A", 14B", 14C", 14D", 14E", 14F", 14G", 14H" forming a cavity 32A", 32B", 32C", 32D", 32E", 32F", 32G", 32H" with the second element.

In one embodiment represented in FIGS. 6A, 6A' and 6A", the microfluidic device comprises one first element 11A, 11A', 11A" devoid of any recess, the groove 24A, 24A', 24A" is covered by the hydrogel layer 14A, 14A', 14A". The second element 16A, 16A', 16A" comprises a recess within which the hydrogel layer is housed. The first element is in annular contact with the second element. The first element 11A, 11A', 11A" and the second element 16A, 16A', 16A" are made of a single piece.

The width of the recess comprised in said side of the second element 16A, 16A', 16A" is wider than the width of the groove 24A, 24A', 24A" comprised in one side of the first element 11A, 11A', 11A". In particular, the width of the recess comprised in said side of the second element 16A, 16A', 16A" is determined to allow the hydrogel layer 14A, 14A', 14A" to be arranged inside the recess (i.e. the surface area of the hydrogel layer doesn't extend beyond the width of the recess comprised in said side of the second element 16A, 16A', 16A") so that the hydrogel layer 14A, 14A', 14A" is not squeezed (or does not experience pressure) between the first element 11A, 11A', 11A" and the second element 16A, 16A', 16A".

The depth or height of the recess comprised in said side of the second element is greater than the total thickness of the hydrogel layer so as to create a cavity between the second face of the hydrogel layer and the second element.

In an embodiment represented in FIGS. 6B, 6B' and 6B", the first element 11B, 11B', 11B" is devoid of any recess. The second element 16B, 16B', 16B" comprises a first piece 13B, 13B', 13B" and a second piece 17B, 17B', 17B" is employed to deepen or increase the depth or height of the cavity 32B, 32B', 32B" between the second face of the hydrogel layer 14B, 14B', 14B"" and the second element 16B, 16B', 16B". As shown in these figures, the recess within which the hydrogel layer is mounted is defined the first piece 13B and the second piece 17B.

In another embodiment represented in FIGS. 6C, 6C' and 6C" that is similar to the preceding embodiment, the second piece 17C, 17C', 17C" of the second element 16B, 16B', 16B" does not comprise a recess. The hydrogel layer 14C, 14C', 14C" is disposed within the inner boundary of the second piece 13C, 13C', 13C" of the second element 16C, 16C', 16C".

In a particular embodiment shown in FIGS. 6D, 6D' and 6D", the first element 11D, 11D', 11D", that is single piece made, comprises a recess having a bottom comprising at least one groove 24D, 24D', 24D", the hydrogel 14D, 14D', 14D" layer being applied onto said bottom and covering said at least one groove 24D, 24D', 24D" so as to form said at least one microchannel. In one embodiment, the recess opens out on an annular surface that is applied onto said second element 16D, 16D', 16D" to form said at least one cavity located opposite to said at least one microchannel.

The size of the hydrogel layer 14D, 14D', 14D" is configured so that it fits within the outer boundary of the recess. The hydrogel layer 14D, 14D', 14D" applied onto the bottom of the recess and covalently bound thereto stays flat and does not invade the space of the microchannel or touch the inner walls of the microchannel.

According to one embodiment of the invention represented in FIGS. 6D, 6D' and 6D", the recess is formed within the first element 11D, 11D', 11D" and its depth is advantageously greater than the total thickness of one or more hydrogel layers, which allows for the formation of a cavity between the second face of the hydrogel and the second element which is planar.

According to another embodiment of the invention represented in FIGS. 6E, 6E' and 6E", the depth of the recess of the first element 11E, 11E', 11E" is configured so that the thickness of the hydrogel layer(s) 14E, 14E', 14E" fits within said depth of the recess (i.e. the thickness of the hydrogel layer(s) is almost the same or slightly lower than the depth of the recess). The second element may also comprise a recess facing the second face of the hydrogel layer 14E, 14E', 14E".

In one embodiment represented in FIGS. 6F, 6F', 6F", the hydrogel layer 14F, 14F', 14F" is partially mounted within a recess of the first element 11F, 11F', 11F" and within a recess of the second element 16F, 16F', 16F". In such case, the second face of the hydrogel layer may be in contact with said bottom of the recess of the first element 11F, 11F', 11F" and the bottom of the second element 16F, 16F', 16F". The first face of the hydrogel layer is in contact with (and covalently bound to) the bottom of the recess of the first element. The second face of the hydrogel layer may or may not be covalently bound to the bottom of the recess of the second element. As it is clearly shown, the bottom of the recess of the first element comprises a groove and of the bottom of the recess comprises a hollow space that defines with the second face of the hydrogel layer 14F, 14F', 14F" the cavity 32F, 32F', 32F".

In another embodiment shown in FIGS. 6G, 6G' and 6G", the first element 11G, 11G', 11G" does not comprise a recess (only comprises at least one groove) and the second element comprises a recess having a bottom comprising at least one hollow space. The size of the hydrogel layer is configured so that it fits within the outer boundary of said recess comprised in the second element. The hydrogel layer may be covalently bound to the second element or both the first and the second elements.

The microfluidic device of the invention comprises at least one pair of microchannel (on the first face of the hydrogel layer)/cavity (on the second face of the hydrogel layer along the same axis of said microchannel). The microfluidic device of the invention may also comprise multiple pairs of microchannel/cavity. In one embodiment, the device comprises several pairs of microchannel/cavity (see, for example, Figure A"). In another embodiment, the device comprises several microchannels for the one cavity (see, for example, Figure A'). The presence of the multiple pairs or microchannel/cavity enables high throughput screening of various assays. The elastic modulus (or shear modulus) of the hydrogel layer must be sufficient so that the variation of pressure in a pair does not affect the neighbouring pairs.

The FIG. 6H corresponds to a similar embodiment previously described in relation to the FIGS. 4A and 4B but also represent the embodiments of FIG. 6H' and FIG. 6H".

At last, it should be understood that the recess may be formed within one of the first element or the second element or partially within the first element and the second element. Moreover, the first element may comprise one single piece or several pieces assembled together and the same applies to the second element.

The invention claimed is:

1. A microfluidic device (10) comprising:
a) a first element (11) comprising one or more types of chemical functional groups on its surface, wherein said one or more types of the chemical functional groups are comprised in molecules covalently bound to said surface;
b) a hydrogel layer (14) having a first face (7) and a second face (9) located opposite to each other, said hydrogel layer (14) comprising one or more types of chemical functional groups, at least one type of said chemical functional groups is effective to react with at least one type of the chemical functional groups comprised in the molecules covalently bound to the surface of the first element (11); and
c) a second element (16),
wherein the hydrogel layer (14) is interposed between the first element (11) and the second element (16) in a given axis (40) substantially perpendicular to the hydrogel layer (14) and wherein the first element (11), the second element (16) and the hydrogel layer (14) have shapes and dimensions determined to delineate at least one microchannel (34) between the first element (11) and the first face (7) of the hydrogel layer (14) and at least one cavity (32) between the second element (16) and the second face (9) of the hydrogel (14), said at least one microchannel (34) and said at least one cavity (32) being arranged relative to each other so that said given axis (40) intercepts both said at least one microchannel (34) and said at least one cavity (32); and
wherein at least one type of said chemical functional groups comprised in the molecules covalently bound to the surface of the first element (11) and at least one type of said chemical functional groups of the hydrogel layer (14) are covalently bound to each other.

2. The microfluidic device (10) of claim 1, wherein a surface of the second element (16) facing the hydrogel layer (14) comprises one or more types of chemical functional groups and at least one type of said chemical functional groups is covalently bound to at least one type of the chemical functional groups of the hydrogel layer (14).

3. The microfluidic device (10) of claim 1, wherein at least one of the first element (11) and second element (16) comprises a recess (20) within which the hydrogel layer (14) is mounted.

4. The microfluidic device (10) of claim 1, wherein the hydrogel layer (14) covers at least one groove formed onto said surface of said first element (11) so as to form at least one microchannel (34).

5. The microfluidic device (10) of claim 3, wherein said recess (20) is formed on said first element (11) and comprises a bottom (22) having said at least one groove.

6. The microfluidic device (10) according to claim 1, wherein the microfluidic device also comprises means (46) for creating a pressure differential between said at least one microchannel (34) and said at least one cavity (32).

7. The microfluidic device (10) of claim 1, wherein the first element, the second element or both elements comprise(s) polydimethylsiloxane (PDMS).

8. The microfluidic device (10) of claim 1, wherein the chemical functional groups comprised in the molecules covalently bound to at least a portion of the surface of the first element (11) or the second element (16) comprise thiol groups and the chemical functional groups comprised in the hydrogel layer (14) comprise vinylsulfone groups.

9. The microfluidic device (10) of claim 1, wherein the hydrogel layer (14) has an elastic modulus in the range from 1 kPa to 50 kPa.

10. The microfluidic device (10) of claim 1, wherein the hydrogel layer (14) has a thickness in the range from 30 µm to 500 µm.

11. The microfluidic device (10) of claim 1, wherein the device comprises two or more layers of hydrogel.

12. The microfluidic device (10) of claim 1, wherein the hydrogel layer (14) comprises a polymeric matrix comprising one or more macromonomers having hydrophilic functional groups attached to the polymeric backbone of said one or more macromonomers, or one or more macromonomers of hydrophilic nature, and optionally wherein the polymeric matrix comprises polyethylene glycol (PEG).

13. The microfluidic device (10) of claim 12, wherein the polymeric matrix comprising one or more macromonomers comprises vinylsulfone groups or thiol groups or both groups with thiol groups in a molar excess in a range of 0 to 10% relative to vinylsulfone groups.

14. The microfluidic device of claim 1, wherein the hydrogel layer comprises microstructures or micropatterns.

15. The microfluidic device (10) of claim 1, wherein at least one type of cell adhesion molecules is present on the first face (7) of the hydrogel layer (14), on the second face (9) of the hydrogel layer (14), in the bulk of the hydrogel layer (14) or any combination thereof.

16. The microfluidic device of claim 15, wherein the cell adhesion molecules are covalently attached to at least one type of the chemical functional groups of the hydrogel layer.

17. The microfluidic device of claim 16, wherein the cell adhesion molecules are tagged with fc antibody fragment or modified with a heterobifunctional protein crosslinking reagent, such as a heterobifunctional NHS-PEG-maleimide linker.

18. The microfluidic device of claim 15, wherein the cell adhesion molecules comprise any one of fibronectin, collagen, laminin or any combination thereof.

19. The microfluidic device (10) of claim 15, wherein cells are deposited on the cell adhesion molecules on the first face (7) of the hydrogel layer (14), on the second face (9) of the hydrogel layer (14), in the bulk of the hydrogel layer (14) or any combination thereof.

20. The microfluidic device of claim 19, wherein the first face (7) of the hydrogel layer (14), the second face (9) of the hydrogel layer (14), the bulk of the hydrogel layer (14) or any combination thereof contains identical or different types of cells.

21. The microfluidic device of claim 19, wherein the cells form one or more layers.

22. The microfluidic device of claim 18, wherein the cells comprise mammalian cells, in particular human cells.

23. A method for producing a microfluidic device (10) according to claim 1 comprising:
    a) producing or providing the first element (11) and the second element (16);
    b) functionalizing a surface of the first element (11) with molecules comprising one or more types of chemical functional groups;
    c) optionally functionalizing a surface of the second element (16) with molecules comprising one or more types of chemical functional groups;
    d) producing or providing a hydrogel layer (14) containing one or more types of chemical functional groups effective to react with at least one type of the chemical functional groups of the molecules on the surface of the first element (11) or the second element (16) or both elements;
    e) placing the hydrogel layer (14) between the first element (11) and the second element (16);
    f) allowing at least one type of the chemical functional groups of the molecules on the surface(s) of the first element (11), the second element (16) or both elements to covalently react with at least one type of the chemical functional groups of the hydrogel layer (14).

24. The method of claim 23, wherein the hydrogel layer (14) is produced by crosslinking vinylsulfone functionalized polyethylene glycol (PEG-VS) macromonomers and thiol functionalized polyethylene glycol (PEG-SH) macromonomers.

25. A method for actuating the hydrogel layer (14) of the microfluidic device (10) according to claim 1, comprising:
    a) introducing a liquid or gas in at least one microchannel (34) between the first element (11) and the first face (7) of the hydrogel layer (14);
    b) introducing a liquid or gas in at least one cavity (32) between the second element (16) and the second face (9) of the hydrogel layer (14);
    c) flowing said liquid or gas through said at least one microchannel (34) between the first element (11) and the first face (7) of the hydrogel layer (14);
    d) flowing said liquid or gas through said at least one cavity (32) between the second element (16) and the second face (9) of the hydrogel layer (14); and
    adjusting or varying the flow rate of said liquid or the pressure of said gas in said at least one microchannel (34) or said at least one cavity (32) so as to create a pressure differential between said at least one microchannel (34) and said at least one cavity (32), which causes the hydrogel layer (14) to expand or retract by alternatively flexing or bending towards said at least one microchannel (34) or said at least one cavity (32) in two opposite directions normal to the plane of the hydrogel layer.

* * * * *